US009247989B2

(12) United States Patent
Truckai

(10) Patent No.: US 9,247,989 B2
(45) Date of Patent: Feb. 2, 2016

(54) MOISTURE TRANSPORT SYSTEM FOR CONTACT ELECTROCOAGULATION

(71) Applicant: Cytyc Surgical Products, Marlborough, MA (US)

(72) Inventor: Csaba Truckai, Sunnyvale, CA (US)

(73) Assignee: Cytyc Surgical Products, Marlborough, MA (US)

( * ) Notice: Subject to any disclaimer, the term of this patent is extended or adjusted under 35 U.S.C. 154(b) by 0 days.

(21) Appl. No.: 14/635,957

(22) Filed: Mar. 2, 2015

(65) Prior Publication Data

US 2015/0164578 A1   Jun. 18, 2015

Related U.S. Application Data

(60) Continuation of application No. 14/278,741, filed on May 15, 2014, now Pat. No. 8,998,898, which is a continuation of application No. 13/962,178, filed on Aug. 8, 2013, now Pat. No. 9,095,348, which is a (Continued)

(51) Int. Cl.
*A61B 18/18*   (2006.01)
*A61B 18/14*   (2006.01)

(Continued)

(52) U.S. Cl.
CPC .............. *A61B 18/1482* (2013.01); *A61B 17/42* (2013.01); *A61B 18/14* (2013.01);

(Continued)

(58) Field of Classification Search
CPC ............ A61B 2018/00577; A61B 2018/00559
USPC .............................. 606/41; 607/101, 105, 138
See application file for complete search history.

(56) References Cited

U.S. PATENT DOCUMENTS 552,832 A   1/1896   Fort
725,731 A   4/1903   Linn (Continued)

FOREIGN PATENT DOCUMENTS

DE          384246       10/1923
DE         22 22 820    11/1973

(Continued)

OTHER PUBLICATIONS

"Essure, Permanent Birth Control by Conceptus: What is Essure?" Product Information Sheet [on-line] [retrieved Oct. 19, 2004] Retrieved from the Internet: < URL: http://www.essure.com/consumer/c.sub.--what.sub.--is.sub.--essure.aspx >.

(Continued)

*Primary Examiner* — Joseph Stoklosa
*Assistant Examiner* — Jocelyn D Ram
(74) *Attorney, Agent, or Firm* — Robert P. Smith

(57) ABSTRACT

An apparatus and method for use in performing ablation or coagulation of organs and other tissue includes a metallized fabric electrode array which is substantially absorbent and/or permeable to moisture and gases such as steam and conformable to the body cavity. Following placement of the ablation device into contact with the tissue to be ablated, an RF generator is used to deliver RF energy to the conductive regions and to thereby induce current flow from the electrodes to tissue to be ablated. As the current heats the tissue, moisture (such as steam or liquid) leaves the tissue causing the tissue to dehydrate. Suction may be applied to facilitate moisture removal. The moisture permeability and/or absorbency of the electrode carrying member allows the moisture to leave the ablation site so as to prevent the moisture from providing a path of conductivity for the current.

19 Claims, 18 Drawing Sheets

Related U.S. Application Data continuation of application No. 12/581,506, filed on Oct. 19, 2009, now Pat. No. 8,506,563, which is a continuation of application No. 10/959,771, filed on Oct. 6, 2004, now Pat. No. 7,604,633, which is a division of application No. 09/103,072, filed on Jun. 23, 1998, now Pat. No. 6,813,520.

(60) Provisional application No. 60/084,791, filed on May 8, 1998.

(51) Int. Cl.
*A61M 16/04* (2006.01)
*A61B 17/22* (2006.01)
*A61B 17/42* (2006.01)
*A61B 18/00* (2006.01)
*A61B 18/12* (2006.01)
*A61B 19/00* (2006.01)

(52) U.S. Cl.
CPC ............ *A61B18/1485* (2013.01); *A61B 18/18* (2013.01); *A61B 19/40* (2013.01); *A61M 16/0481* (2014.02); *A61B 2017/22051* (2013.01); *A61B 2017/4216* (2013.01); *A61B 2018/00291* (2013.01); *A61B 2018/00559* (2013.01); *A61B 2018/00577* (2013.01); *A61B 2018/00708* (2013.01); *A61B 2018/126* (2013.01); *A61B 2019/4009* (2013.01); *A61B 2019/465* (2013.01)

(56) References Cited

U.S. PATENT DOCUMENTS

| | | |
|---|---|---|
| 1,620,929 A | 3/1927 | Wallerich |
| 1,827,306 A | 10/1931 | Chapman et al. |
| 2,190,383 A | 2/1940 | Newman |
| 2,347,195 A | 4/1944 | Huff |
| 2,466,042 A | 4/1949 | Reich et al. |
| 3,228,398 A | 1/1966 | Leonard et al. |
| 3,324,855 A | 6/1967 | Heimlich |
| 3,645,265 A | 2/1972 | Majzlin |
| 3,706,307 A | 12/1972 | Hasson |
| 3,840,016 A | 10/1974 | Lindemann |
| 3,845,771 A | 11/1974 | Vise |
| 3,858,586 A | 1/1975 | Lessen |
| 3,877,464 A | 4/1975 | Vermes |
| 3,924,628 A | 12/1975 | Droegemueller et al. |
| 3,948,270 A | 4/1976 | Hasson |
| 3,967,625 A | 7/1976 | Yoon |
| 3,971,378 A | 7/1976 | Krantz |
| 4,016,867 A * | 4/1977 | King et al. .................... 600/591 |
| 4,022,215 A | 5/1977 | Benson |
| 4,057,063 A | 11/1977 | Gieles et al. |
| 4,082,096 A | 4/1978 | Benson |
| 4,094,320 A | 6/1978 | Newton et al. |
| 4,158,050 A | 6/1979 | Zipper |
| 4,185,618 A | 1/1980 | Corey |
| 4,224,951 A | 9/1980 | Hasson |
| 4,233,025 A | 11/1980 | Larson et al. |
| 4,347,842 A | 9/1982 | Beale |
| 4,359,454 A | 11/1982 | Hoffman |
| 4,380,238 A | 4/1983 | Colucci et al. |
| 4,415,288 A | 11/1983 | Gordon et al. |
| 4,449,528 A | 5/1984 | Auth et al. |
| 4,465,072 A | 8/1984 | Taheri |
| 4,489,732 A | 12/1984 | Hasson |
| 4,492,231 A | 1/1985 | Auth |
| 4,532,483 A | 7/1985 | Schminke |
| 4,532,924 A | 8/1985 | Auth et al. |
| 4,552,557 A | 11/1985 | Rangaswamy |
| 4,568,326 A | 2/1986 | Rangaswamy |
| 4,582,057 A | 4/1986 | Auth et al. |
| 4,601,698 A | 7/1986 | Moulding, Jr. |
| 4,606,336 A | 8/1986 | Zeluff |
| 4,628,924 A | 12/1986 | Cimber |
| 4,662,383 A | 5/1987 | Sogawa et al. |
| 4,676,258 A | 6/1987 | Inokuchi et al. |
| 4,685,474 A | 8/1987 | Kurz et al. |
| 4,691,703 A | 9/1987 | Auth et al. |
| 4,700,701 A | 10/1987 | Montaldi |
| 4,739,759 A | 4/1988 | Rexroth et al. |
| 4,765,331 A | 8/1988 | Petruzzi et al. |
| 4,788,966 A | 12/1988 | Yoon |
| 4,807,620 A | 2/1989 | Strul et al. |
| 4,832,048 A | 5/1989 | Cohen |
| 4,865,047 A | 9/1989 | Chou et al. |
| 4,869,268 A | 9/1989 | Yoon |
| 4,946,440 A | 8/1990 | Hall |
| 4,949,718 A | 8/1990 | Neuwirth et al. |
| 4,955,377 A | 9/1990 | Lennox et al. |
| 4,960,133 A | 10/1990 | Hewson |
| 4,961,435 A | 10/1990 | Kitagawa et al. |
| 4,979,948 A | 12/1990 | Geddes et al. |
| 4,981,465 A | 1/1991 | Ballan et al. |
| 4,983,177 A | 1/1991 | Wolf |
| 5,026,379 A | 6/1991 | Yoon |
| 5,047,028 A | 9/1991 | Qian |
| 5,057,106 A | 10/1991 | Kasevich et al. |
| 5,065,751 A | 11/1991 | Wolf |
| 5,078,717 A | 1/1992 | Parins et al. |
| 5,084,044 A | 1/1992 | Quint |
| 5,105,808 A | 4/1992 | Neuwirth et al. |
| 5,109,869 A | 5/1992 | Buckley |
| 5,147,353 A | 9/1992 | Everett |
| 5,159,925 A | 11/1992 | Neuwirth et al. |
| 5,160,334 A | 11/1992 | Billings et al. |
| 5,178,148 A | 1/1993 | Lacoste et al. |
| 5,186,181 A | 2/1993 | Franconi et al. |
| 5,188,122 A | 2/1993 | Phipps et al. |
| 5,188,602 A | 2/1993 | Nichols |
| 5,217,473 A | 6/1993 | Yoon |
| 5,226,908 A | 7/1993 | Yoon |
| 5,242,437 A | 9/1993 | Everett et al. |
| 5,248,312 A | 9/1993 | Langberg |
| 5,263,585 A | 11/1993 | Lawhon et al. |
| 5,275,610 A | 1/1994 | Eberbach |
| 5,277,201 A | 1/1994 | Stern |
| 5,308,327 A | 5/1994 | Heaven et al. |
| 5,318,532 A | 6/1994 | Frassica |
| 5,322,507 A | 6/1994 | Costello et al. |
| 5,334,193 A | 8/1994 | Nardella |
| 5,334,209 A | 8/1994 | Yoon |
| 5,354,295 A | 10/1994 | Guglielmi et al. |
| 5,357,956 A | 10/1994 | Nardella |
| 5,358,496 A * | 10/1994 | Ortiz et al. .................... 606/198 |
| 5,364,393 A | 11/1994 | Auth et al. |
| 5,370,649 A | 12/1994 | Gardetto et al. |
| 5,374,261 A | 12/1994 | Yoon |
| 5,374,283 A | 12/1994 | Flick |
| 5,380,317 A | 1/1995 | Everett et al. |
| 5,383,917 A | 1/1995 | Desai et al. |
| 5,385,544 A | 1/1995 | Edwards et al. |
| 5,395,311 A | 3/1995 | Andrews |
| 5,405,322 A | 4/1995 | Lennox et al. |
| 5,407,071 A | 4/1995 | Lawhon et al. |
| 5,423,808 A | 6/1995 | Edwards et al. |
| 5,433,708 A | 7/1995 | Nichols et al. |
| 5,437,629 A | 8/1995 | Goldrath |
| 5,443,470 A | 8/1995 | Stern et al. |
| 5,451,204 A * | 9/1995 | Yoon .................. 604/1 |
| 5,474,089 A | 12/1995 | Waynant |
| 5,484,400 A | 1/1996 | Edwards et al. |
| 5,498,261 A | 3/1996 | Strul |
| 5,505,730 A * | 4/1996 | Edwards ........................ 606/41 |
| 5,507,743 A | 4/1996 | Edwards et al. |
| 5,514,091 A | 5/1996 | Yoon |
| 5,540,655 A | 7/1996 | Edwards et al. |
| 5,540,681 A | 7/1996 | Strul et al. |
| 5,542,916 A | 8/1996 | Hirsch et al. |
| 5,558,672 A | 9/1996 | Edwards et al. |
| 5,562,703 A | 10/1996 | Desai |
| 5,562,720 A | 10/1996 | Stern et al. |

(56) References Cited

U.S. PATENT DOCUMENTS

| | | | |
|---|---|---|---|
| 5,573,533 A | 11/1996 | Strul | |
| 5,575,788 A | 11/1996 | Baker et al. | |
| 5,588,961 A | 12/1996 | Leone et al. | |
| 5,593,404 A | 1/1997 | Costello et al. | |
| 5,599,345 A | 2/1997 | Edwards et al. | |
| 5,599,346 A | 2/1997 | Edwards et al. | |
| 5,609,598 A | 3/1997 | Laufer et al. | |
| 5,613,950 A | 3/1997 | Yoon | |
| 5,620,481 A | 4/1997 | Desai et al. | |
| 5,649,924 A | 7/1997 | Everett et al. | |
| 5,656,013 A | 8/1997 | Yoon | |
| 5,658,316 A | 8/1997 | Lamond et al. | |
| 5,667,520 A | 9/1997 | Bonutti | |
| 5,697,882 A | 12/1997 | Eggers et al. | |
| 5,702,438 A * | 12/1997 | Avitall | 607/122 |
| 5,716,343 A | 2/1998 | Kriesel et al. | |
| 5,722,975 A | 3/1998 | Edwards et al. | |
| 5,730,136 A | 3/1998 | Laufer et al. | |
| 5,730,725 A | 3/1998 | Yoon | |
| 5,733,252 A | 3/1998 | Yoon | |
| 5,769,880 A | 6/1998 | Truckai et al. | |
| 5,779,698 A | 7/1998 | Clayman et al. | |
| 5,797,903 A | 8/1998 | Swanson et al. | |
| 5,800,482 A | 9/1998 | Pomeranz et al. | |
| 5,807,389 A | 9/1998 | Gardetto et al. | |
| 5,810,847 A | 9/1998 | Laufer et al. | |
| 5,827,273 A | 10/1998 | Edwards | |
| 5,843,026 A | 12/1998 | Edwards et al. | |
| 5,843,121 A | 12/1998 | Yoon | |
| 5,846,238 A | 12/1998 | Jackson et al. | |
| 5,865,788 A | 2/1999 | Edwards et al. | |
| 5,871,469 A | 2/1999 | Eggers et al. | |
| 5,879,348 A | 3/1999 | Owens et al. | |
| 5,885,278 A | 3/1999 | Fleischman | |
| 5,885,601 A | 3/1999 | Sokal | |
| 5,888,198 A | 3/1999 | Eggers et al. | |
| 5,891,134 A | 4/1999 | Goble et al. | |
| 5,891,136 A | 4/1999 | McGee et al. | |
| 5,897,551 A | 4/1999 | Everett et al. | |
| 5,897,553 A | 4/1999 | Mulier et al. | |
| 5,935,123 A | 8/1999 | Edwards et al. | |
| 5,935,137 A | 8/1999 | Saadat et al. | |
| 5,938,660 A | 8/1999 | Swartz et al. | |
| 5,944,715 A | 8/1999 | Goble et al. | |
| 5,954,717 A | 9/1999 | Behl et al. | |
| 5,979,446 A | 11/1999 | Loy | |
| 5,997,534 A | 12/1999 | Tu et al. | |
| 6,002,968 A | 12/1999 | Edwards | |
| 6,014,589 A | 1/2000 | Farley et al. | |
| 6,033,397 A | 3/2000 | Laufer et al. | |
| 6,036,687 A | 3/2000 | Laufer et al. | |
| 6,041,260 A | 3/2000 | Stern et al. | |
| 6,042,596 A | 3/2000 | Bonutti | |
| 6,047,700 A | 4/2000 | Eggers et al. | |
| 6,066,139 A | 5/2000 | Ryan et al. | |
| 6,068,613 A | 5/2000 | Kriesel et al. | |
| 6,068,626 A | 5/2000 | Harrington et al. | |
| 6,071,277 A | 6/2000 | Farley et al. | |
| 6,071,281 A | 6/2000 | Burnside et al. | |
| 6,074,386 A | 6/2000 | Goble et al. | |
| 6,077,257 A | 6/2000 | Edwards et al. | |
| 6,096,052 A | 8/2000 | Callister et al. | |
| 6,112,123 A | 8/2000 | Kelleher et al. | |
| 6,117,101 A | 9/2000 | Diederich et al. | |
| 6,123,702 A | 9/2000 | Swanson et al. | |
| 6,135,997 A | 10/2000 | Laufer et al. | |
| 6,139,527 A | 10/2000 | Laufer et al. | |
| 6,139,546 A | 10/2000 | Koenig et al. | |
| 6,152,899 A | 11/2000 | Farley et al. | |
| 6,159,207 A | 12/2000 | Yoon | |
| 6,164,280 A | 12/2000 | Everett et al. | |
| 6,165,172 A | 12/2000 | Farley et al. | |
| 6,179,832 B1 | 1/2001 | Jones et al. | |
| 6,183,468 B1 | 2/2001 | Swanson et al. | |
| 6,193,713 B1 | 2/2001 | Geistert et al. | |
| 6,197,025 B1 | 3/2001 | Grossi et al. | |
| 6,200,312 B1 | 3/2001 | Zikorus et al. | |
| 6,224,591 B1 | 5/2001 | Claren et al. | |
| 6,231,496 B1 | 5/2001 | Wilk et al. | |
| 6,231,507 B1 | 5/2001 | Zikorus et al. | |
| 6,234,178 B1 | 5/2001 | Goble et al. | |
| 6,237,606 B1 | 5/2001 | Zikorus et al. | |
| 6,238,393 B1 | 5/2001 | Mulier et al. | |
| 6,245,065 B1 | 6/2001 | Panescu et al. | |
| 6,245,090 B1 | 6/2001 | Gilson et al. | |
| 6,254,601 B1 | 7/2001 | Burbank et al. | |
| 6,258,084 B1 | 7/2001 | Goldman et al. | |
| 6,258,085 B1 | 7/2001 | Eggleston | |
| 6,263,248 B1 | 7/2001 | Farley et al. | |
| 6,277,089 B1 | 8/2001 | Yoon | |
| 6,293,942 B1 | 9/2001 | Goble et al. | |
| 6,296,639 B1 | 10/2001 | Truckai et al. | |
| 6,309,384 B1 | 10/2001 | Harrington et al. | |
| 6,315,776 B1 | 11/2001 | Edwards et al. | |
| 6,322,559 B1 | 11/2001 | Daulton et al. | |
| 6,346,102 B1 | 2/2002 | Harrington et al. | |
| 6,352,549 B1 | 3/2002 | Everett | |
| 6,364,877 B1 | 4/2002 | Goble et al. | |
| 6,369,465 B1 | 4/2002 | Swanson | |
| 6,395,012 B1 | 5/2002 | Yoon et al. | |
| 6,398,780 B1 | 6/2002 | Farley et al. | |
| 6,402,742 B1 | 6/2002 | Blewett et al. | |
| 6,428,537 B1 | 8/2002 | Swanson et al. | |
| 6,432,116 B1 | 8/2002 | Callister et al. | |
| 6,451,015 B1 | 9/2002 | Rittman, III et al. | |
| 6,475,213 B1 | 11/2002 | Whayne et al. | |
| 6,485,487 B1 | 11/2002 | Sherman | |
| 6,485,500 B1 | 11/2002 | Kokish et al. | |
| 6,490,474 B1 | 12/2002 | Willis et al. | |
| 6,508,815 B1 | 1/2003 | Strul et al. | |
| 6,554,780 B1 | 4/2003 | Sampson et al. | |
| 6,663,626 B2 | 12/2003 | Truckai et al. | |
| 6,679,269 B2 | 1/2004 | Swanson | |
| 6,712,810 B2 | 3/2004 | Harrington et al. | |
| 6,712,815 B2 | 3/2004 | Sampson et al. | |
| 6,726,682 B2 | 4/2004 | Harrington et al. | |
| 6,743,184 B2 | 6/2004 | Sampson et al. | |
| 6,764,488 B1 | 7/2004 | Burbank et al. | |
| 6,813,520 B2 | 11/2004 | Truckai et al. | |
| 6,964,274 B1 | 11/2005 | Ryan et al. | |
| 7,074,217 B2 | 7/2006 | Strul et al. | |
| 7,407,502 B2 | 8/2008 | Strul et al. | |
| 7,512,445 B2 | 3/2009 | Truckai et al. | |
| 7,604,633 B2 | 10/2009 | Truckai et al. | |
| 7,717,909 B2 | 5/2010 | Strul et al. | |
| 7,731,712 B2 | 6/2010 | Sampson et al. | |
| 7,846,160 B2 | 12/2010 | Payne et al. | |
| 2001/0041900 A1 | 11/2001 | Callister et al. | |
| 2002/0022870 A1 | 2/2002 | Truckai et al. | |
| 2002/0029051 A1 | 3/2002 | Callister et al. | |
| 2002/0072499 A1 | 6/2002 | Clagett | |
| 2002/0072745 A1 | 6/2002 | Truckai et al. | |
| 2002/0177846 A1 | 11/2002 | Mulier et al. | |
| 2003/0093101 A1 | 5/2003 | O'Heeron et al. | |
| 2003/0130711 A1 | 7/2003 | Pearson et al. | |
| 2003/0199863 A1 | 10/2003 | Swanson et al. | |
| 2004/0054368 A1 | 3/2004 | Truckai et al. | |
| 2004/0118166 A1 | 6/2004 | Huang et al. | |
| 2004/0172051 A1 | 9/2004 | Ravikumar | |
| 2004/0204720 A1 | 10/2004 | Harrington et al. | |
| 2004/0255958 A1 | 12/2004 | Harrington et al. | |
| 2005/0085880 A1 | 4/2005 | Truckai et al. | |
| 2005/0155608 A1 | 7/2005 | Pavcnik et al. | |
| 2005/0217680 A1 | 10/2005 | Callister et al. | |
| 2006/0135956 A1 | 6/2006 | Sampson et al. | |
| 2008/0071269 A1 | 3/2008 | Hilario et al. | |
| 2010/0036372 A1 | 2/2010 | Truckai et al. | |
| 2010/0217256 A1 | 8/2010 | Strul et al. | |
| 2012/0179155 A1 | 7/2012 | Strul et al. | |

FOREIGN PATENT DOCUMENTS

| | | |
|---|---|---|
| DE | 40 01 086 | 7/1991 |
| EP | 0 056 178 | 4/1981 |

(56) References Cited

FOREIGN PATENT DOCUMENTS

| | | |
|---|---|---|
| EP | 0 584 930 | 7/1993 |
| EP | 1 400 182 | 3/2004 |
| EP | 1 568 325 | 8/2005 |
| FR | 774 550 | 12/1934 |
| FR | 2 115 706 | 7/1972 |
| GB | 2 317 566 | 4/1998 |
| JP | 48-67586 | 12/1971 |
| JP | 58-32756 | 2/1983 |
| JP | 63-318934 | 12/1988 |
| WO | 92/19145 | 11/1992 |
| WO | 94/00178 | 1/1994 |
| WO | 94/07445 | 4/1994 |
| WO | 94/10948 | 5/1994 |
| WO | 94/23794 | 10/1994 |
| WO | 95/04385 | 2/1995 |
| WO | 95/05869 | 3/1995 |
| WO | 95/07664 | 3/1995 |
| WO | 95/10326 | 4/1995 |
| WO | 96/00042 | 1/1996 |
| WO | 97/12569 | 4/1997 |
| WO | 97/41785 | 11/1997 |
| WO | 98/38932 | 9/1998 |
| WO | 99/58070 | 11/1999 |
| WO | 01/97897 | 12/2001 |

OTHER PUBLICATIONS

"Essure: the non-incisional approach to permanent birth control", Patient Information Booklet, .COPYRGT. 2004 by Conceptus Incorporated.

"Tubal Ligation and Resection: Tubal Ligation by Parkland and Irving Methods" Datasheet [on-line] Chapel Hill Tubal Reversal Center, 2004 [retrieved on Oct. 19, 2004] Retrieved from the Internet: <URL: http://www.tubal-reversal.net/print/printer-friendly-tubal.sub.--ligation- .sub.--resection.htm >.

"Tubal Ligation Methods: Coagulation Methods of Tubal Ligation" Datasheet [on-line] Chapel Hill Tubal Reversal Center, 2004, [retrieved Oct. 19, 2004] Retrieved from the Internet: < http://www.tubal-reversal.net/tubal.sub.--ligation. sub.--coagulation.htm >.

"Tubal Ligation—Fimbriectomy: Tubal Reversal is Possible after Fimbriectomy" Datasheet [on-line] Chapel Hill Tubal Reversal Center, 2004 [retrieved on Oct. 19, 2004] Retrieved from the Internet: <URL: http://www.tubal-reversal.net/print/printer-friendly-tubal.sub.--ligation- .sub.--fimbriectomy.htm >.

"Tubal Ligation—Pomeroy Technique: Pomeroy Tubal Ligation and Resection" Datasheet [on-line] Chapel Hill Tubal Reversal Center, 2004 [retrieved Oct. 19, 2004 ] Retrieved from the Internet: < http://www.tubal-reversal.net/print/printer-friendly-tubal.sub.--ligation- .sub.--Pomeroy.htm >.

"Tubal Ligation—Tubal Ring or Clip: Tubal Ligation with Tubal Rings or Tubal Clips" Datasheet [on-line] Chapel Hill Tubal Reversal Center, 2004 [retrieved Oct. 19, 2004] Retrieved from the Internet: <URL: http://www.tubal-reversal.net/tubal.sub.--ligation-tubal.sub.--ring-tubal- .sub.--clip.htm >.

Adiana options for women—how it works. (Dec. 31, 2005). Retrieved from http://web.archive.org/web/20051124001429/www.adiana.com/products.sub.--h- ow.php.

C. Nibley et al., "Prevention of Impedance Rise During Radiofrequency Current Catheter Ablation by Intra-Electrode Tip Chilling," Circulation [Abstracts From the 67th Scientific Sessions, Dallas Convention Center, Dallas, Texas, Nov. 14-17, 1994], vol. 90, No. 4, Part 2, Oct. 1994, p. 460.

D.E. Haines et al., "Observations on Electrode-Tissue Interface Temperature and Effect on Electrical Impedance During Radiofrequency Ablation on Ventricular Myocardium," Circulation, vol. 82, No. 3, Sep. 1990, pp. 1034-1038.

METI-MyriadLase, SteriLase, Powerpoint Presentation, published at least as of Jun. 13, 2006, 6 pp.

W.M. Jackman et al., "Radiofrequency Current Directed Across the Mitral Anulus With a Bipolar Epicardial-Endocardial Catheter Electrode Configuration in Dogs," Circulation, vo. 78, No. 5, Nov. 1988, pp. 1288-1298.

First Request for Ex Partes Reexamination of U.S. Pat. No. 5,769,880, filed Jul. 27, 1999, U.S. Appl. No. 90/005,435.

Second Request for Ex Partes Reexamination of U.S. Pat. No. 5,769,880, filed Nov. 22, 2000, U.S. Appl. No. 90/005,866.

Complaint pending in the U.S. District Court for the District of Delaware under Civil Action No. 1:15-cv-01031-UNA, filed by Hologic, Inc., et al. against Minerva, Inc. on Nov. 6, 2015, of Infringement of U.S. Pat. No. 6,872,183 issued Mar. 29, 2005, U.S. Pat. No. 8,998,898 issued Apr. 7, 2015, and U.S. Pat. No. 9,095,348 issued Aug. 4, 2015, 144 pages.

* cited by examiner

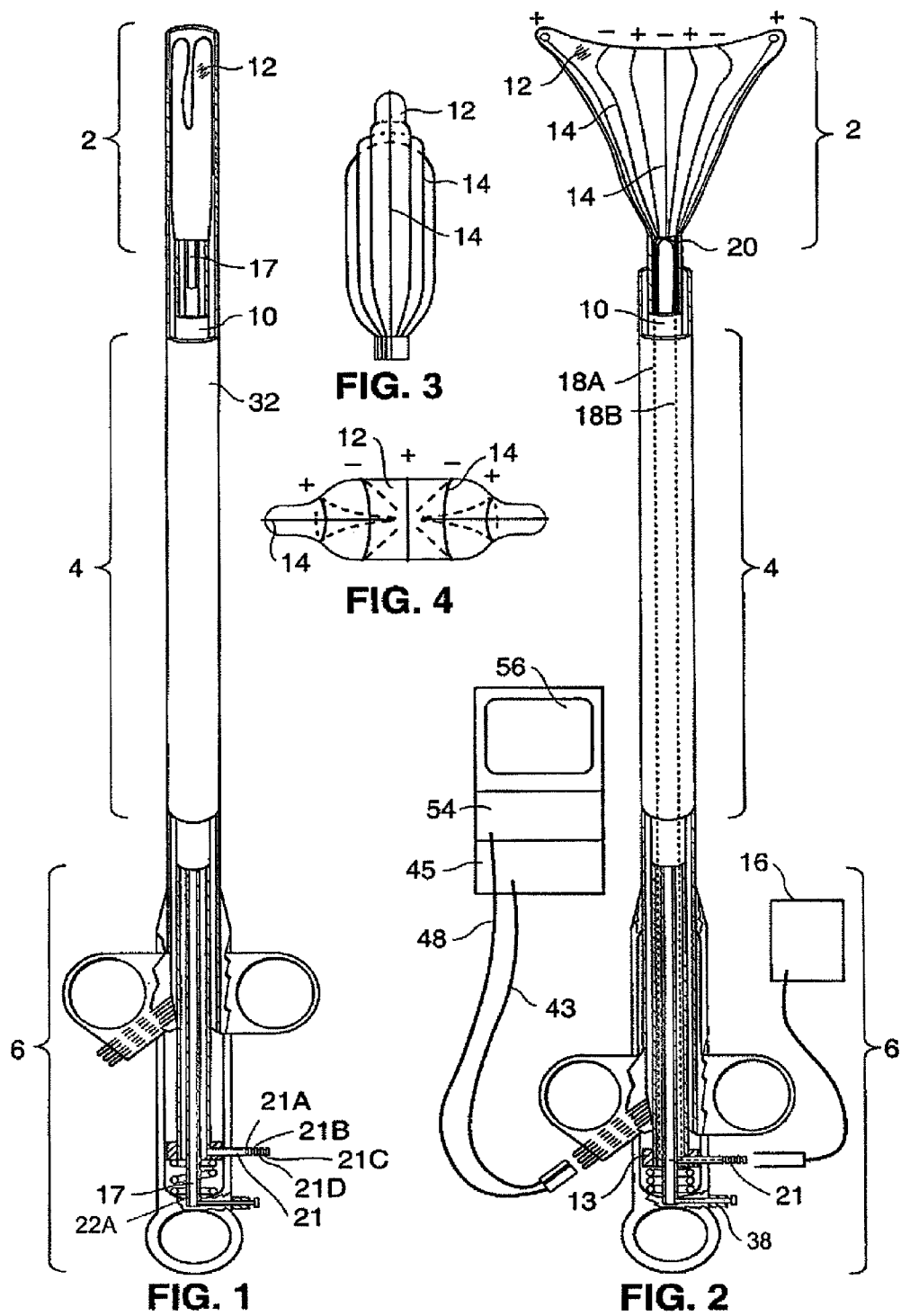

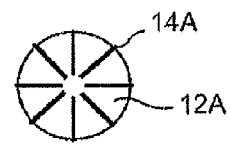
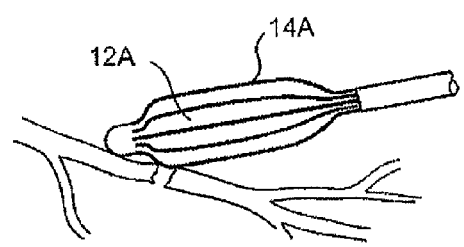
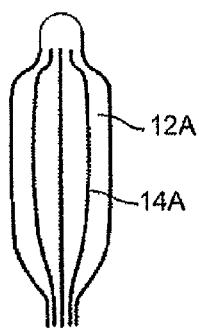
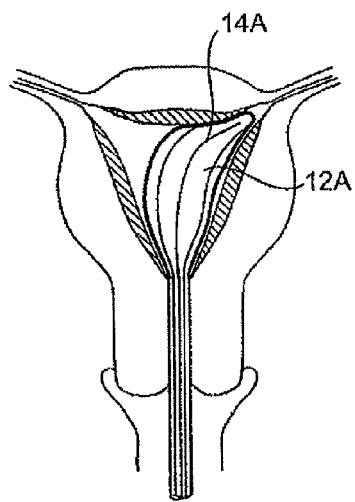
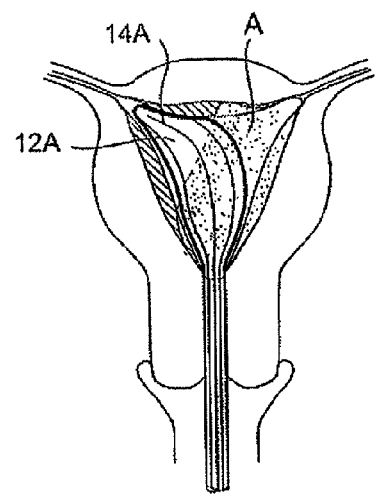
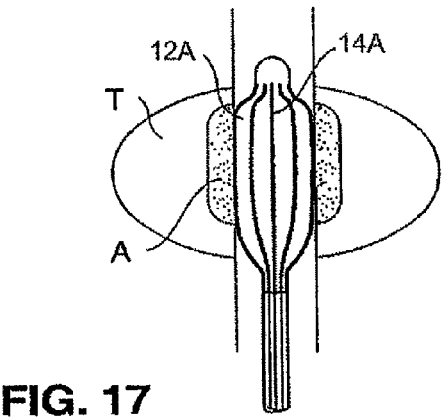

US 9,247,989 B2

MOISTURE TRANSPORT SYSTEM FOR CONTACT ELECTROCOAGULATION

RELATED APPLICATIONS

This application is a continuation of U.S. application Ser. No. 14/278,741 filed May 15, 2014, now U.S. Pat. No. 8,998,898, which is a continuation of pending U.S. application Ser. No. 13/962,178 filed Aug. 8, 2013, which is a continuation of U.S. application Ser. No. 12/581,506 filed Oct. 19, 2009, now U.S. Pat. No. 8,506,563, which is a continuation of U.S. application Ser. No. 10/959,771 filed Oct. 6, 2004, now U.S. Pat. No. 7,604,633, which is a divisional of U.S. application Ser. No. 09/103,072 filed Jun. 23, 1998, now U.S. Pat. No. 6,813,520, which claims the benefit of U.S. provisional application 60/084,791 filed May 8, 1998.

FIELD OF THE INVENTION

The present invention relates generally to the field of apparatuses and methods for ablating or coagulating the interior surfaces of body organs. Specifically, it relates to an apparatus and method for ablating the interior linings of body organs such as the uterus and gallbladder.

BACKGROUND OF THE INVENTION

Ablation of the interior lining of a body organ is a procedure which involves heating the organ lining to temperatures which destroy the cells of the lining or coagulate tissue proteins for hemostasis. Such a procedure may be performed as a treatment to one of many conditions, such as chronic bleeding of the endometrial layer of the uterus or abnormalities of the mucosal layer of the gallbladder. Existing methods for effecting ablation include circulation of heated fluid inside the organ (either directly or inside a balloon), laser treatment of the organ lining, and resistive heating using application of RF energy to the tissue to be ablated.

U.S. Pat. No. 5,084,044 describes an apparatus for endometrial ablation in which a bladder is inserted into the uterus. Heated fluid is then circulated through the balloon to expand the balloon into contact with the endometrium and to ablate the endometrium thermally. U.S. Pat. No. 5,443,470 describes an apparatus for endometrial ablation in which an expandable bladder is provided with electrodes on its outer surface. After the apparatus is positioned inside the uterus, a non-conductive gas or liquid is used to fill the balloon, causing the balloon to push the electrodes into contact with the endometrial surface. RF energy is supplied to the electrodes to ablate the endometrial tissue using resistive heating.

These ablation devices are satisfactory for carrying out ablation procedures. However, because no data or feedback is available to guide the physician as to how deep the tissue ablation has progressed, controlling the ablation depth and ablation profile with such devices can only be done by assumption.

For example, the heated fluid method is a very passive and ineffective heating process which relies on the heat conductivity of the tissue. This process does not account for variations in factors such as the amount of contact between the balloon and the underlying tissue, or cooling effects such as those of blood circulating through the organ. RF ablation techniques can achieve more effective ablation since it relies on active heating of the tissue using RF energy, but presently the depth of ablation using RF techniques can only be estimated by the physician since no feedback can be provided as to actual ablation depth.

Both the heated fluid techniques and the latest RF techniques must be performed using great care to prevent over ablation. Monitoring of tissue surface temperature is normally carried out during these ablation procedures to ensure the temperature does not exceed 100° C. If the temperature exceeds 100° C., the fluid within the tissue begins to boil and to thereby produce steam. Because ablation is carried out within a closed cavity within the body, the steam cannot escape and may instead force itself deeply into the tissue, or it may pass into areas adjacent to the area intended to be ablated, causing embolism or unintended burning.

Moreover, in prior art RF devices the water drawn from the tissue creates a path of conductivity through which current traveling through the electrodes will flow. This can prevent the current from traveling into the tissue to be ablated. Moreover, the presence of this current path around the electrodes causes current to be continuously drawn from the electrodes. The current heats the liquid drawn from the tissue and thus turns the ablation process into a passive heating method in which the heated liquid around the electrodes causes thermal ablation to continue well beyond the desired ablation depths.

Another problem with prior art ablation devices is that it is difficult for a physician to find out when ablation has been carried out to a desired depth within the tissue. Thus, it is often the case that too much or too little tissue may be ablated during an ablation procedure.

It is therefore desirable to provide an ablation device which eliminates the above-described problem of steam and liquid buildup at the ablation site. It is further desirable to provide an ablation method and device which allows the depth of ablation to be controlled and which automatically discontinues ablation once the desired ablation depth has been reached.

SUMMARY OF THE INVENTION

The present invention is an apparatus and method of ablating and/or coagulating tissue, such as that of the uterus or other organ. An ablation device is provided which has an electrode array carried by an elongate tubular member. The electrode array includes a fluid permeable elastic member preferably formed of a metallized fabric having insulating regions and conductive regions thereon. During use, the electrode array is positioned in contact with tissue to be ablated, ablation energy is delivered through the array to the tissue to cause the tissue to dehydrate, and moisture generated during dehydration is actively or passively drawn into the array and away from the tissue.

BRIEF DESCRIPTION OF THE DRAWINGS

FIG. 1 is a front elevation view of a first embodiment of an ablation device according to the present invention, with the handle shown in cross-section and with the RF applicator head in a closed condition.

FIG. 2 is a front elevation view of the ablation device of FIG. 1, with the handle shown in cross-section and with the RF applicator head in an open condition.

FIG. 3 is a side elevation view of the ablation device of FIG. 2.

FIG. 4 is a top plan view of the ablation device of FIG. 2.

FIG. 12 is a side elevation view of the distal end of an alternate embodiment of an RF ablation device similar to that of FIG. 1, which utilizes an RF applicator head having a modified shape.

FIG. 13 is a top plan view of the ablation device of FIG. 12.

FIG. 14 is a representation of a bleeding vessel illustrating use of the ablation device of FIG. 12 for general bleeding control.

FIGS. 15 and 16 are representations of a uterus illustrating use of the ablation device of FIG. 12 for endometrial ablation.

FIG. 17 is a representation of a prostate gland illustrating use of the ablation device of FIG. 12 for prostate ablation.

FIG. 37A shows the condition of the compression spring before the heel member moves into abutment with frame member, and FIG. 37B shows the condition of the spring after the heel member moves into abutment with the frame member.

DETAILED DESCRIPTION

Figures 5A, 5B:
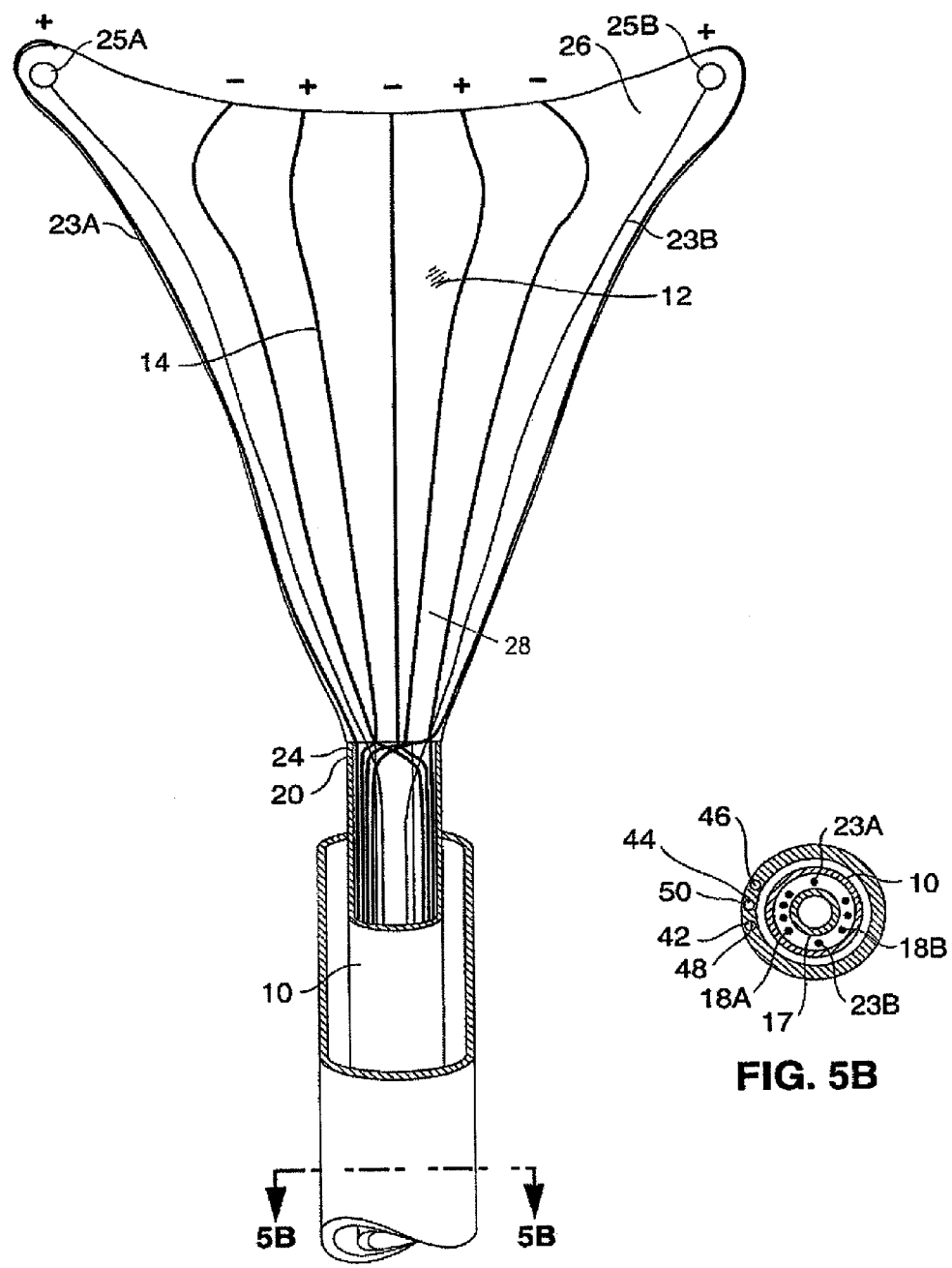
FIG. 5A is a front elevation view of the applicator head and a portion of the main body of the ablation device of FIG. 2, with the main body shown in cross-section.
FIG. 5B is a cross-section view of the main body taken along the plane designated 5B-5B in FIG. 5A.

The invention described in this application is an aspect of a larger set of inventions described in the following co-pending applications which are commonly owned by the assignee of the present invention, and are hereby incorporated by reference: U.S. Provisional Patent Application No. 60/084,724, filed May 8, 1998, entitled "APPARATUS AND METHOD FOR INTRA-ORGAN MEASUREMENT AND ABLATION"; and U.S. Provisional Patent Application No. 60/084,712 filed May 8, 1998, entitled "A RADIO-FREQUENCY GENERATOR FOR POWERING AN ABLATION DEVICE".

The ablation apparatus according to the present invention will be described with respect to two exemplary embodiments.

First Exemplary Embodiment—Structure

Referring to FIGS. 1 and 2, an ablation device according to the present invention is comprised generally of three major components: RF applicator head 2, main body 4, and handle 6. Main body 4 includes a shaft 10. The RF applicator head 2 includes an electrode carrying means 12 mounted to the distal end of the shaft 10 and an array of electrodes 14 formed on the surface of the electrode carrying means 12. An RF generator 16 is electrically connected to the electrodes 14 to provide mono-polar or bipolar RF energy to them.

Figure 6:
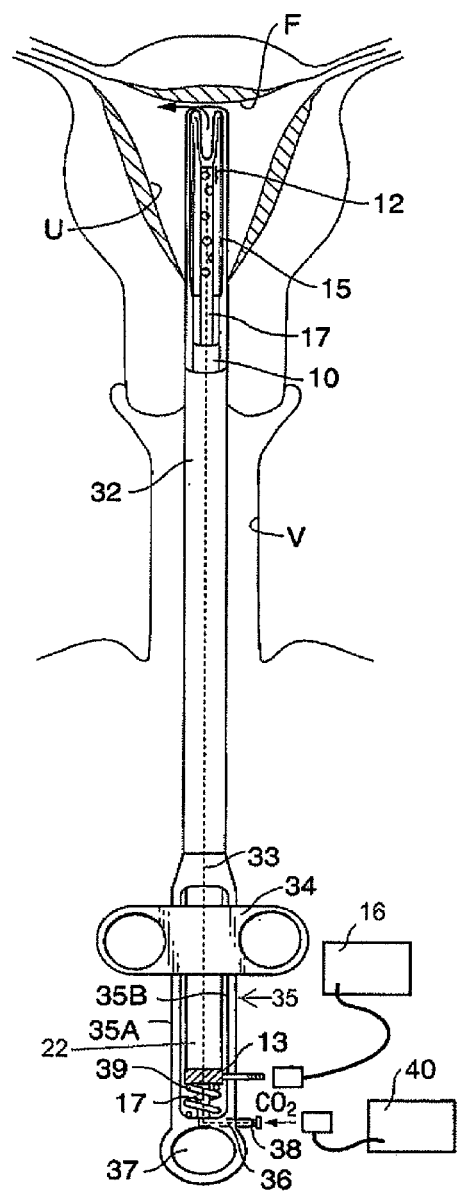
FIG. 6 is a schematic representation of a uterus showing the ablation device of FIG. 1 following insertion of the device into the uterus but prior to retraction of the introducer sheath and activation of the spring members.
Figure 7:
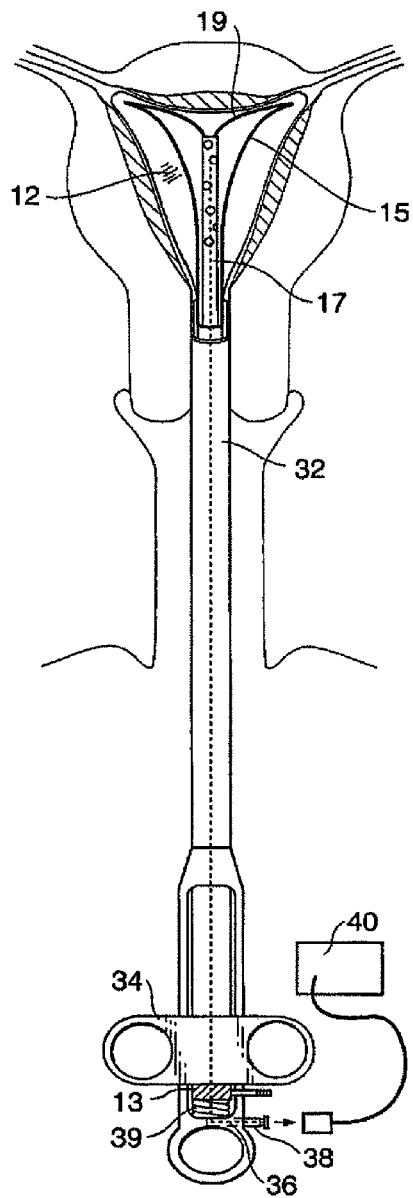
FIG. 7 is a schematic representation of a uterus showing the ablation device of FIG. 1 following insertion of the device into the uterus and following the retraction of the introducer sheath and the expansion of the RF applicator head.
Figure 8:
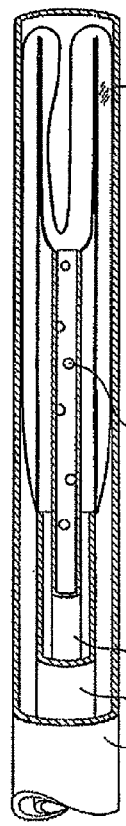
FIG. 8 is a cross-section view of the RF applicator head and the distal portion of the main body of the apparatus of FIG. 1, showing the RF applicator head in the closed condition.
Figure 9:
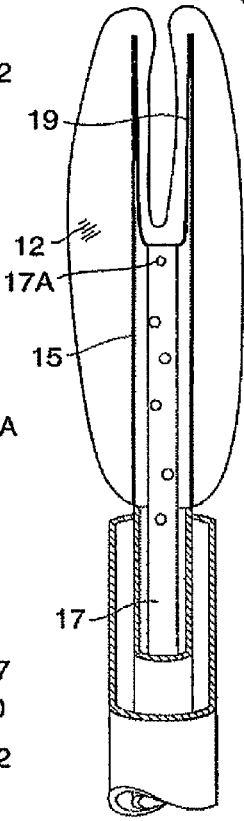
FIG. 9 is a cross-section view of the RF applicator head and the distal portion of the main body of the apparatus of FIG. 1, showing the configuration of RF applicator head after the sheath has been retracted but before the spring members have been released by proximal movement of the shaft.
Figure 10:
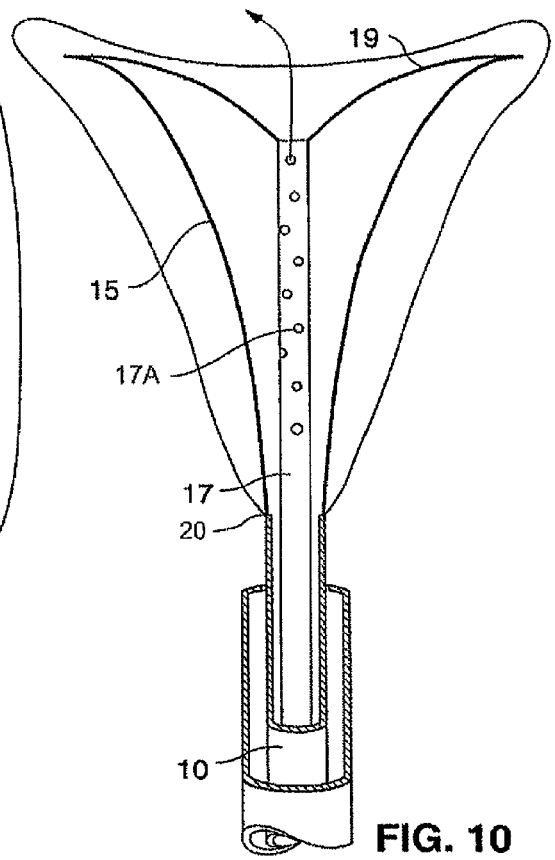
FIG. 10 is a cross-section view of the RF applicator head and the distal portion of the main body of the apparatus of FIG. 1, showing the configuration of RF applicator head after the sheath has been retracted and after the spring members have been released into the fully opened condition.

Shaft 10 is an elongate member having a hollow interior. Shaft 10 is preferably 12 inches long and has a preferred cross-sectional diameter of approximately 4 mm. A collar 13 is formed on the exterior of the shaft 10 at the proximal end. As best shown in FIGS. 6 and 7, passive spring member 15 are attached to the distal end of the shaft 10.

Extending through the shaft 10 is a suction/insufflation tube 17 (FIGS. 6-9) having a plurality of holes 17a formed in its distal end. An arched active spring member 19 is connected between the distal ends of the passive spring members 15 and the distal end of the suction/insufflation tube 17.

Referring to FIG. 2, electrode leads 18a and 18b extend through the shaft 10 from distal end 20 to proximal end 22 of the shaft 10. At the distal end 20 of the shaft 10, each of the leads 18a, 18b is coupled to a respective one of the electrodes 14. At the proximal end 22 of the shaft 10, the leads 18a, 18b are electrically connected to RF generator 16 via an electrical connector 21. During use, the leads 18a, 18b carry RF energy from the RF generator 16 to the electrodes. Each of the leads 18a, 18b is insulated and carries energy of an opposite polarity than the other lead.

Electrically insulated sensor leads 23a, 23b (FIGS. 5A and 5B) also extend through the shaft 10. Contact sensors 25a, 25b are attached to the distal ends of the sensor leads 23a, 23b, respectively and are mounted to the electrode carrying means 12. During use, the sensor leads 23a, 23b are coupled by the connector 21 to a monitoring module in the RF generator 16 which measures impedance between the sensors 25a, 25b. Alternatively, a reference pad may be positioned in contact with the patient and the impedance between one of the sensors and the reference pad measured.

Referring to FIG. 5B, electrode leads 18a, 18b and sensor leads 23a, 23b extend through the shaft 10 between the external walls of the tube 17 and the interior walls of the shaft 10 and they are coupled to electrical connector 21 which is preferably mounted to the collar 13 on the shaft 10. Connector 21, which is connectable to the RF generator 16, includes at least four electrical contact rings 21a-21d (FIGS. 1 and 2) which correspond to each of the leads 18a, 18b, 23a, 23b. Rings 21a, 21b receive, from the RF generator, RF energy of positive and negative polarity, respectively. Rings 21c, 21d deliver signals from the right and left sensors, respectively, to a monitoring module within the RF generator 16.

Referring to FIG. 5A, the electrode carrying means 12 is attached to the distal end 20 of the shaft 10. A plurality of holes 24 may be formed in the portion of the distal end 20 of the shaft which lies within the electrode carrying means 12.

The electrode carrying means 12 preferably has a shape which approximates the shape of the body organ which is to be ablated. For example, the apparatus shown in FIGS. 1 through 11 has a bicornual shape which is desirable for intrauterine ablation. The electrode carrying means 12 shown in these figures includes horn regions 26 which during use are positioned within the cornual regions of the uterus and which therefore extend towards the fallopian tubes.

Electrode carrying means 12 is preferably a sack formed of a material which is non-conductive, which is permeable to moisture and/or which has a tendency to absorb moisture, and which may be compressed to a smaller volume and subsequently released to its natural size upon elimination of compression. Examples of preferred materials for the electrode carrying means include open cell sponge, foam, cotton, fabric, or cotton-like material, or any other material having the desired characteristics. Alternatively, the electrode carrying means may be formed of a metallized fabric. For convenience, the term "pad" may be used interchangeably with the term electrode carrying means to refer to an electrode carrying means formed of any of the above materials or having the listed properties.

Electrodes 14 are preferably attached to the outer surface of the electrode carrying means 12, such as by deposition or other attachment mechanism. The electrodes are preferably made of lengths of silver, gold, platinum, or any other conductive material. The electrodes may be attached to the electrode carrying means 12 by electron beam deposition, or they may be formed into coiled wires and bonded to the electrode carrying member using a flexible adhesive. Naturally, other means of attaching the electrodes, such as sewing them onto the surface of the carrying member, may alternatively be used. If the electrode carrying means 12 is formed of a metallized fabric, an insulating layer may be etched onto the fabric surface, leaving only the electrode regions exposed.

The spacing between the electrodes (i.e. the distance between the centers of adjacent electrodes) and the widths of the electrodes are selected so that ablation will reach predetermined depths within the tissue, particularly when maximum power is delivered through the electrodes (where maximum power is the level at which low impedance, low voltage ablation can be achieved).

The depth of ablation is also effected by the electrode density (i.e., the percentage of the target tissue area which is in contact with active electrode surfaces) and may be regulated by pre-selecting the amount of this active electrode coverage. For example, the depth of ablation is much greater when the active electrode surface covers more than 10% of the target tissue than it is when the active electrode surfaces covers 1% of the target tissue.

For example, by using 3-6 mm spacing and an electrode width of approximately 0.5-2.5 mm, delivery of approximately 20-40 watts over a 9-16 cm2 target tissue area will cause ablation to a depth of approximately 5-7 millimeters when the active electrode surface covers more than 10% of the target tissue area. After reaching this ablation depth, the impedance of the tissue will become so great that ablation will self-terminate as described with respect to the operation of the invention.

By contrast, using the same power, spacing, electrode width, and RF frequency will produce an ablation depth of only 2-3 mm when the active electrode surfaces covers less than 1% of the target tissue area. This can be better understood with reference to FIG. 19A, in which high surface density electrodes are designated 14a and low surface density electrodes are designated 14b. For purposes of this comparison between low and high surface density electrodes, each bracketed group of low density electrodes is considered to be a single electrode. Thus, the electrode widths W and spacings S extend as shown in FIG. 19A.

Figure 19A:
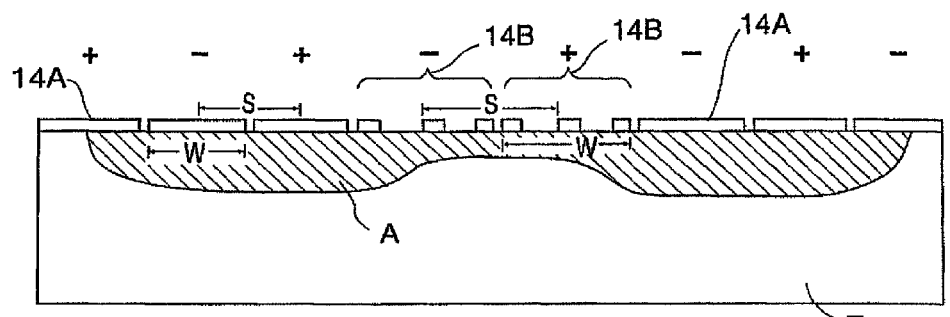
FIGS. 19A-19C are cross-section views of target tissue for ablation, showing electrodes in contact with the tissue surface and illustrating how varying active electrode density may be used to vary the ablation depth.

As is apparent from FIG. 19A, the electrodes 14a, which have more active area in contact with the underlying tissue T, produce a region of ablation A1 that extends more deeply into the tissue T than the ablation region A2 produced by the low density electrodes 14b, even though the electrode spacings and widths are the same for the high and low density electrodes.

Some examples of electrode widths, having spacings with more than 10% active electrode surface coverage, and their resultant ablation depth, based on an ablation area of 6 cm2 and a power of 20-40 watts, are given on the following table:

| ELECTRODE WIDTH | SPACING | APPROX. DEPTH |
| --- | --- | --- |
| 1 mm | 1-2 mm | 1-3 mm |
| 1-2.5 mm | 3-6 mm | 5-7 mm |
| 1-4.5 mm | 8-10 mm | 8-10 mm |

Examples of electrode widths, having spacings with less than 1% active electrode surface coverage, and their resultant ablation depth, based on an ablation area of 6 cm2 and a power of 20-40 watts, are given on the following table:

| ELECTRODE WIDTH | SPACING | APPROX. DEPTH |
| --- | --- | --- |
| 1 mm | 1-2 mm | 0.5-1 mm |
| 1-2.S mm | 3-6 mm | 2-3 mm |
| 1-4.5 mm | 8-10 mm | 2-3 mm |

Thus it can be seen that the depth of ablation is significantly less when the active electrode surface coverage is decreased.

In the preferred embodiment, the preferred electrode spacing is approximately 8-10 mm in the horn regions 26 with the active electrode surfaces covering approximately 1% of the target region. Approximately 1-2 mm electrode spacing (with 10% active electrode coverage) is preferred in the cervical region (designated 28) and approximately 3-6 mm (with greater than 10% active electrode surface coverage) is preferred in the main body region.

The RF generator 16 may be configured to include a controller which gives the user a choice of which electrodes should be energized during a particular application in order to give the user control of ablation depth. For example, during an application for which deep ablation is desired, the user may elect to have the generator energize every other electrode, to thereby optimize the effective spacing of the electrodes and to decrease the percentage of active electrode surface coverage, as will be described below with respect to FIG. 18.

Although the electrodes shown in the drawings are arranged in a particular pattern, it should be appreciated that the electrodes may be arranged in any pattern to provide ablation to desired depths.

Referring to FIGS. 6 and 7, an introducer sheath 32 facilitates insertion of the apparatus into, and removal of the apparatus from, the body organ to be ablated. The sheath 32 is a tubular member which is telescopically slidable over the shaft 10. The sheath 32 is slidable between a distal condition, shown in FIG. 6, in which the electrode carrying means 12 is compressed inside the sheath, and a proximal condition in which the sheath 32 is moved proximally to release the electrode carrying means from inside it (FIG. 7). By compressing the electrode carrying means 12 to a small volume, the electrode carrying means and electrodes can be easily inserted into the body cavity (such as into the uterus via the vaginal opening).

A handle 34 attached to the sheath 32 provides finger holds to allow for manipulation of the sheath 32. Handle 34 is slidably mounted on a handle rail 35 which includes a sleeve 33, a finger cutout 37, and a pair of spaced rails 35a, 35b extending between the sleeve 33 and the finger cutout 37. The shaft 10 and sheath 32 slidably extend through the sleeve 33 and between the rails 35a, 35b. The tube 17 also extends through the sleeve 33 and between the rails 35a, 35b, and its proximal end is fixed to the handle rail 35 near the finger cutout 37.

A compression spring 39 is disposed around the proximal most portion of the suction/insufflation tube 17 which lies between the rails 35a, 35b. One end of the compression spring 39 rests against the collar 13 on the shaft 10, while the opposite end of the compression spring rests against the handle rail 35. During use, the sheath 32 is retracted from the electrode carrying means 12 by squeezing the handle 34 towards the finger cutout 37 to slide the sheath 32 in the distal direction. When the handle 34 advances against the collar 13, the shaft 10 (which is attached to the collar 13) is forced to slide in the proximal direction, causing compression of the spring 39 against the handle rail 35. The movement of the shaft 10 relative to the suction/insufflation tube 17 causes the shaft 10 to pull proximally on the passive spring member 15. Proximal movement of the passive spring member 15 in turn pulls against the active spring member 19, causing it to move to the opened condition shown in FIG. 7. Unless the shaft is held in this retracted condition, the compression spring 39 will push the collar and thus the shaft distally, forcing the RF applicator head to close. A locking mechanism (not shown) may be provided to hold the shaft in the fully withdrawn condition to prevent inadvertent closure of the spring members during the ablation procedure.

The amount by which the springs 15, 19 are spread may be controlled by manipulating the handle 34 to slide the shaft 10 (via collar 13), proximally or distally. Such sliding movement of the shaft 10 causes forceps-like movement of the spring members 15, 19.

A flow pathway 36 is formed in the handle rail 35 and is fluidly coupled to a suction/insufflation port 38. The proximal end of the suction/insufflation tube 17 is fluidly coupled to the flow pathway so that gas fluid may be introduced into, or withdrawn from the suction/insufflation tube 17 via the suction/insufflation port 38. For example, suction may be applied to the fluid port 38 using a suction/insufflation unit 40. This causes water vapor within the uterine cavity to pass through the permeable electrode carrying means 12, into the suction/insufflation tube 17 via holes 17a, through the tube 17, and through the suction/insufflation unit 40 via the port 38. If insufflation of the uterine cavity is desired, insufflation gas, such as carbon dioxide, may be introduced into the suction/insufflation tube 17 via the port 38. The insufflation gas travels through the tube 17, through the holes 17a, and into the uterine cavity through the permeable electrode carrying member 12.

If desirable, additional components may be provided for endoscopic visualization purposes. For example, lumen 42, 44, and 46 may be formed in the walls of the introducer sheath 32 as shown in FIG. 5B. An imaging conduit, such as a fiberoptic cable 48, extends through lumen 42 and is coupled via a camera cable 43 to a camera 45. Images taken from the camera may be displayed on a monitor 56. An illumination fiber 50 extends through lumen 44 and is coupled to an illumination source 54. The third lumen 46 is an instrument channel through which surgical instruments may be introduced into the uterine cavity, if necessary.

Because during use it is most desirable for the electrodes 14 on the surface of the electrode carrying means 12 to be held in contact with the interior surface of the organ to be ablated, the electrode carrying means 12 may be provided to have additional components inside it that add structural integrity to the electrode carrying means when it is deployed within the body.

Figure 11:
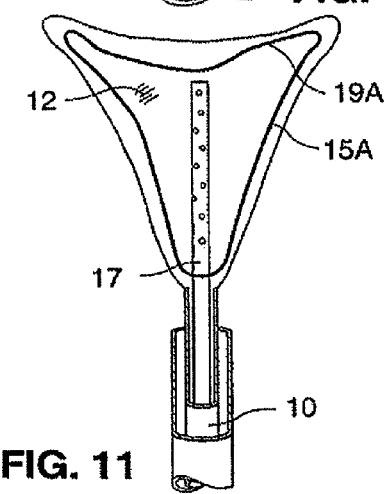
FIG. 11 is a cross-section view of a distal portion of an RF ablation device similar to FIG. 1 which utilizes an alternative spring member configuration for the RF applicator head.

For example, referring to FIG. 11, alternative spring members 15a, 19a may be attached to the shaft 10 and biased such that, when in a resting state, the spring members are positioned in the fully resting condition shown in FIG. 11. Such spring members would spring to the resting condition upon withdrawal of the sheath 32 from the RF applicator head 2.

Figure 20:
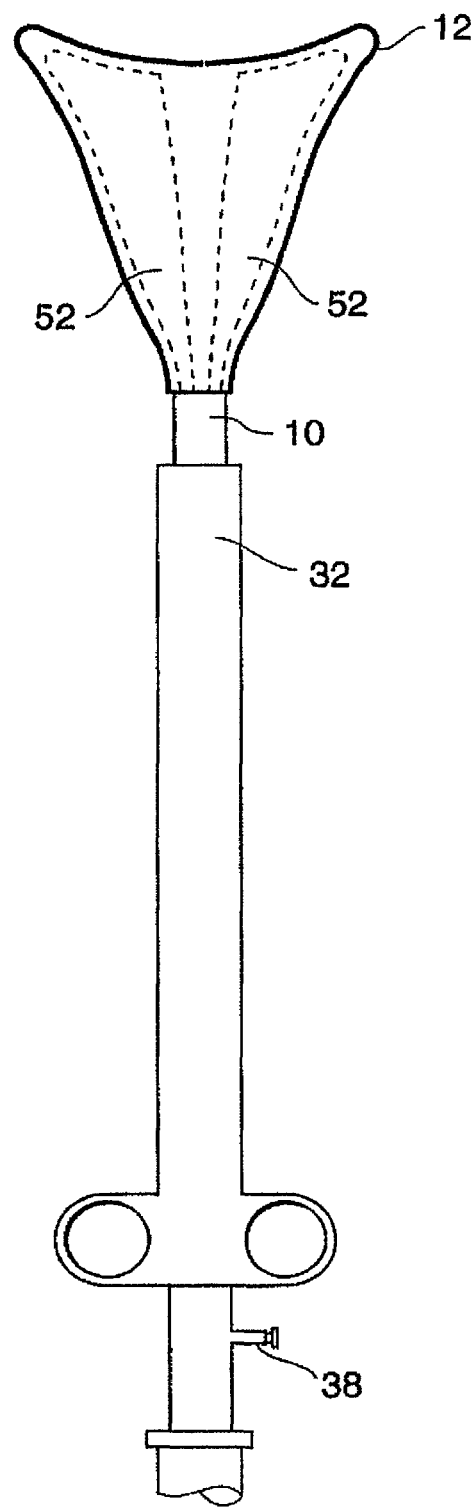
FIG. 20 is a side elevation view, similar to the view of FIG. 2, showing an ablation device according to the present invention in which the electrode carrying means includes inflatable balloons. For purposes of clarity, the electrodes on the electrode carrying means are not shown.

Alternatively, a pair of inflatable balloons 52 may be arranged inside the electrode carrying means 12 as shown in FIG. 20 and connected to a tube (not shown) extending through the shaft 10 and into the balloons 52. After insertion of the apparatus into the organ and following retraction of the sheath 32, the balloons 52 would be inflated by introduction of an inflation medium such as air into the balloons via a port similar to port 38 using an apparatus similar to the suction/insufflation apparatus 40.

Structural integrity may also be added to the electrode carrying means through the application of suction to the proximal end 22a of the suction/insufflation tube 17. Application of suction using the suction/insufflation device 40 would draw the organ tissue towards the electrode carrying means 12 and thus into better contact with the electrodes 14.

FIGS. 12 and 13 show an alternative embodiment of an ablation device according to the present invention. In the alternative embodiment, an electrode carrying means 12a is provided which has a shape which is generally tubular and thus is not specific to any particular organ shape. An ablation device having a general shape such as this may be used anywhere within the body where ablation or coagulation is needed. For example, the alternative embodiment is useful for bleeding control during laparoscopic surgery (FIG. 14), tissue ablation in the prostate gland (FIG. 17), and also intrauterine ablation (FIGS. 15 and 16).

First Exemplary Embodiment—Operation

Operation of the first exemplary embodiment of an ablation device according to the present invention will next be described.

Referring to FIG. 1, the device is initially configured for use by positioning the introducer sheath 32 distally along the shaft 10, such that it compresses the electrode carrying means 12 within its walls.

At this time, the electrical connector 21 is connected to the RF generator 16, and the fiberoptic cable 48 and the illumination cable 50 are connected to the illumination source, monitor, and camera, 54, 56, 45. The suction/insufflation unit 40 is attached to suction/insufflation port 38 on the handle rail 35. The suction/insufflation unit 40 is preferably set to deliver carbon dioxide at an insufflation pressure of 20-200 mmHg.

Next, the distal end of the apparatus is inserted through the vaginal opening V and into the uterus U as shown in FIG. 6, until the distal end of the introducer sheath 32 contacts the fundus F of the uterus. At this point, carbon dioxide gas is introduced into the tube 17 via the port 38, and it enters the uterine cavity, thereby expanding the uterine cavity from a flat triangular shape to a 1-2 cm high triangular cavity. The physician may observe (using the camera 45 and monitor 56) the internal cavities using images detected by a fiberoptic cable 48 inserted through lumen 42. If, upon observation, the physician determines that a tissue biopsy or other procedure is needed, the required instruments may be inserted into the uterine cavity via the instrument channel 46.

Following insertion, the handle 34 is withdrawn until it abuts the collar 13. At this point, the sheath 32 exposes the electrode carrying member 12 but the electrode carrying member 12 is not yet fully expanded (see FIG. 9), because the spring members 15, 19 have not yet been moved to their open condition. The handle 34 is withdrawn further, causing the shaft 10 to move proximally relative to the suction/insufflation tube 17, causing the passive spring members 15 to pull the active spring members 19, causing them to open into the opened condition shown in FIG. 10.

The physician may confirm proper positioning of the electrode carrying member 12 using the monitor 56, which displays images from the fiberoptic cable 48.

Proper positioning of the device and sufficient contact between the electrode carrying member 12 and the endometrium may further be confirmed using the contact sensors 25a, 25b. The monitoring module of the RF generator measures the impedance between these sensors using conventional means. If there is good contact between the sensors and the endometrium, the measured impedance will be approximately 20-180 ohm, depending on the water content of the endometrial lining.

The sensors are positioned on the distal portions of the bicornual shaped electrode carrying member 12, which during use are positioned in the regions within the uterus in which it is most difficult to achieve good contact with the endometrium. Thus, an indication from the sensors 25a, 25b that there is sound contact between the sensors and the endometrial surface indicates that good electrode contact has been made with the endometrium.

Next, insufflation is terminated. Approximately 1-5 cc of saline may be introduced via suction/insufflation tube 17 to initially wet the electrodes and to improve electrode electrical contact with the tissue. After introduction of saline, the suction/insufflation device 40 is switched to a suctioning mode. As described above, the application of suction to the RF applicator head 2 via the suction/insufflation tube 17 collapses the uterine cavity onto the RF applicator head 2 and thus assures better contact between the electrodes and the endometrial tissue.

If the generally tubular apparatus of FIGS. 12 and 13 is used, the device is angled into contact with one side of the uterus during the ablation procedure. Once ablation is completed, the device (or a new device) is repositioned in contact with the opposite side and the procedure is repeated. See. FIGS. 15 and 16.

Figure 18:
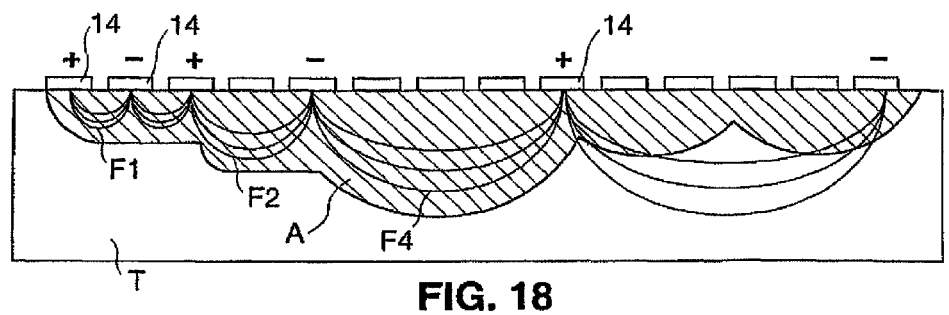
FIG. 18 is a cross-section view of target tissue for ablation, showing ablation electrodes in contact with the tissue surface and illustrating energy fields generated during bi-polar ablation.

Next, RF energy at preferably about 500 kHz and at a constant power of approximately 30 W is applied to the electrodes. As shown in FIG. 5a, it is preferable that each electrode be energized at a polarity opposite from that of its neighboring electrodes. By doing so, energy field patterns, designated F1, F2 and F4 in FIG. 18, are generated between the electrode sites and thus help to direct the flow of current through the tissue T to form a region of ablation A. As can be seen in FIG. 18, if electrode spacing is increased such by energizing, for example every third or fifth electrode rather than all electrodes, the energy patterns will extend more deeply into the tissue. (See, for example, pattern F2 which results from energization of electrodes having a non-energized electrode between them, or pattern F4 which results from energization of electrodes having three non-energized electrodes between them).

Figure 19B:
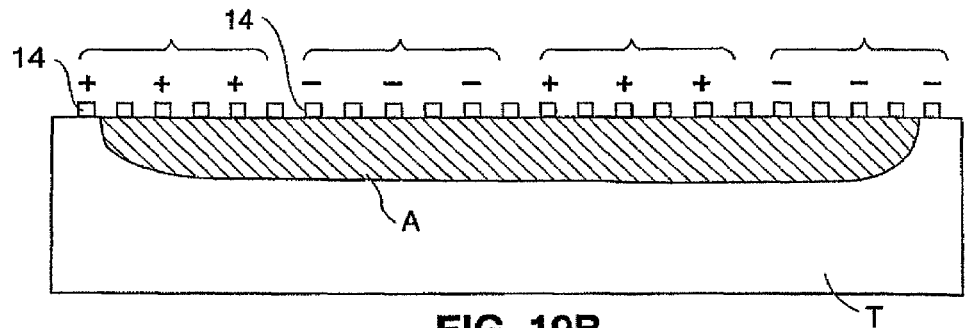

Moreover, ablation depth may be controlled as described above by providing low surface density electrodes on areas of the electrode carrying member which will contact tissue areas at which a smaller ablation depth is required (see FIG. 19A). Referring to FIG. 19B, if multiple, closely spaced, electrodes 14 are provided on the electrode carrying member, a user may set the RF generator to energize electrodes which will produce a desired electrode spacing and active electrode area. For example, alternate electrodes may be energized as shown in FIG. 19B, with the first three energized electrodes having positive polarity, the second three having negative polarity, etc.

Figure 19C:
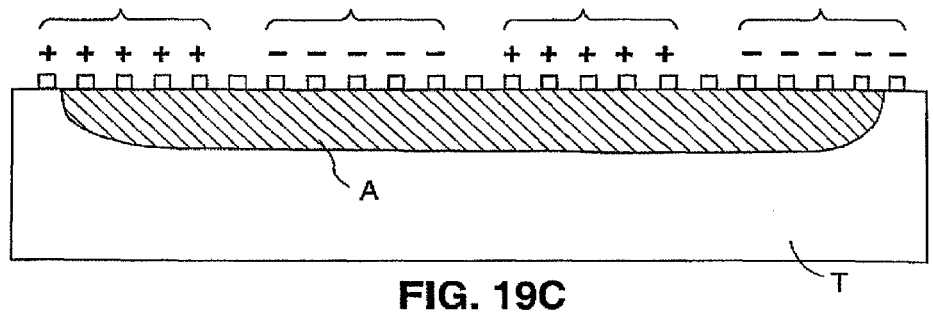

As another example, shown in FIG. 19C, if greater ablation depth is desired the first five electrodes may be positively energized, and the seventh through eleventh electrodes negatively energized, with the sixth electrode remaining inactivated to provide adequate electrode spacing.

As the endometrial tissue heats, moisture begins to be released from the tissue. The moisture permeates the electrode carrying member 12 and is thereby drawn away from the electrodes. The moisture may pass through the holes 17a in the suction/insufflation tube 17 and leave the suction/insufflation tube 17 at its proximal end via port 38 as shown in FIG. 7. Moisture removal from the ablation site may be further facilitated by the application of suction to the shaft 10 using the suction/insufflation unit 40.

Removal of the moisture from the ablation site prevents formation of a liquid layer around the electrodes. As described above, liquid build-up at the ablation site is detrimental in that provides a conductive layer that carries current from the electrodes even when ablation has reached the desired depth. This continued current flow heats the liquid and surrounding tissue, and thus causes ablation to continue by unpredictable thermal conduction means.

Tissue which has been ablated becomes dehydrated and thus decreases in conductivity. By shunting moisture away from the ablation site and thus preventing liquid build-up, there is no liquid conductor at the ablation area during use of the ablation device of the present invention. Thus, when ablation has reached the desired depth, the impedance at the tissue surface becomes sufficiently high to stop or nearly stop the flow of current into the tissue. RF ablation thereby stops and thermal ablation does not occur in significant amounts. If the RF generator is equipped with an impedance monitor, a physician utilizing the ablation device can monitor the impedance at the electrodes and will know that ablation has self-terminated once the impedance rises to a certain level and then remains fairly constant. By contrast, if a prior art bipolar RF ablation device was used together with an impedance monitor, the presence of liquid around the electrodes would cause the impedance monitor to give a low impedance reading regardless of the depth of ablation which had already been carried out, since current would continue to travel through the low-impedance liquid layer.

Other means for monitoring and terminating ablation may also be provided. For example, a thermocouple or other temperature sensor may be inserted to a predetermined depth in the tissue to monitor the temperature of the tissue and terminate the delivery of RF energy or otherwise signal the user when the tissue has reached a desired ablation temperature.

Once the process has self terminated, 1-5 cc of saline can be introduced via suction/insufflation tube 17 and allowed to sit for a short time to aid separation of the electrode from the tissue surface. The suction insufflation device 40 is then switched to provide insufflation of carbon dioxide at a pressure of 20-200 mmHg. The insufflation pressure helps to lift the ablated tissue away from the RF applicator head 2 and to thus ease the closing of the RF applicator head. The RF applicator head 2 is moved to the closed position by sliding the handle 34 in a distal direction to fold the spring members 15, 19 along the axis of the device and to cause the introducer sheath 32 to slide over the folded RF applicator head. The physician may visually confirm the sufficiency of the ablation using the monitor 56. Finally, the apparatus is removed from the uterine cavity.

Second Exemplary Embodiment—Structure

A second embodiment of an ablation device 100 in accordance with the present invention is shown in FIGS. 21-37B. The second embodiment differs from the first embodiment primarily in its electrode pattern and in the mechanism used to deploy the electrode applicator head or array. Naturally, aspects of the first and second exemplary embodiments and their methods of operation may be combined without departing from the scope of the present invention.

Figure 21:
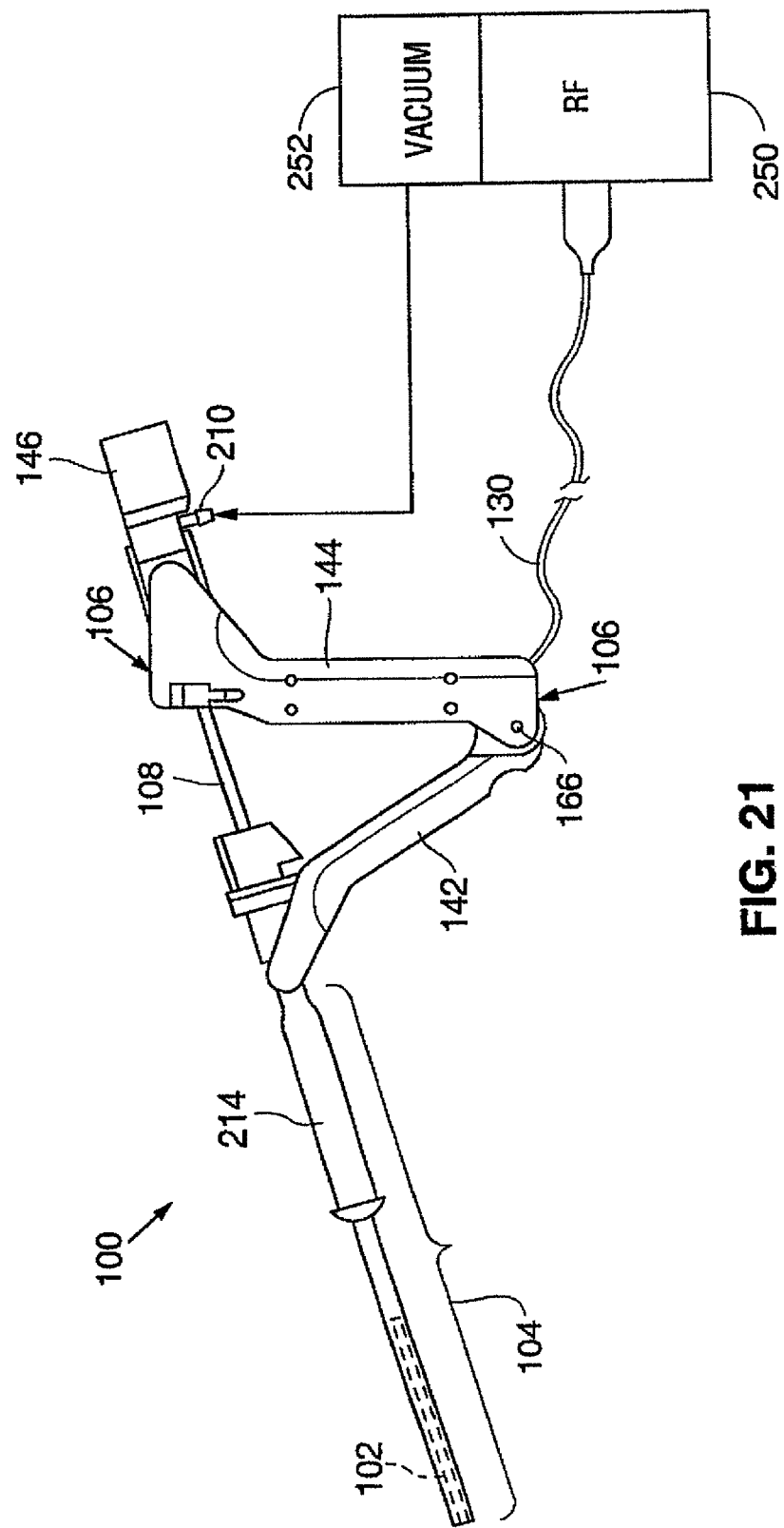
FIG. 21 is a side elevation view of a second exemplary embodiment of an ablation device according to the present invention, showing the array in the retracted state.
Figure 22:
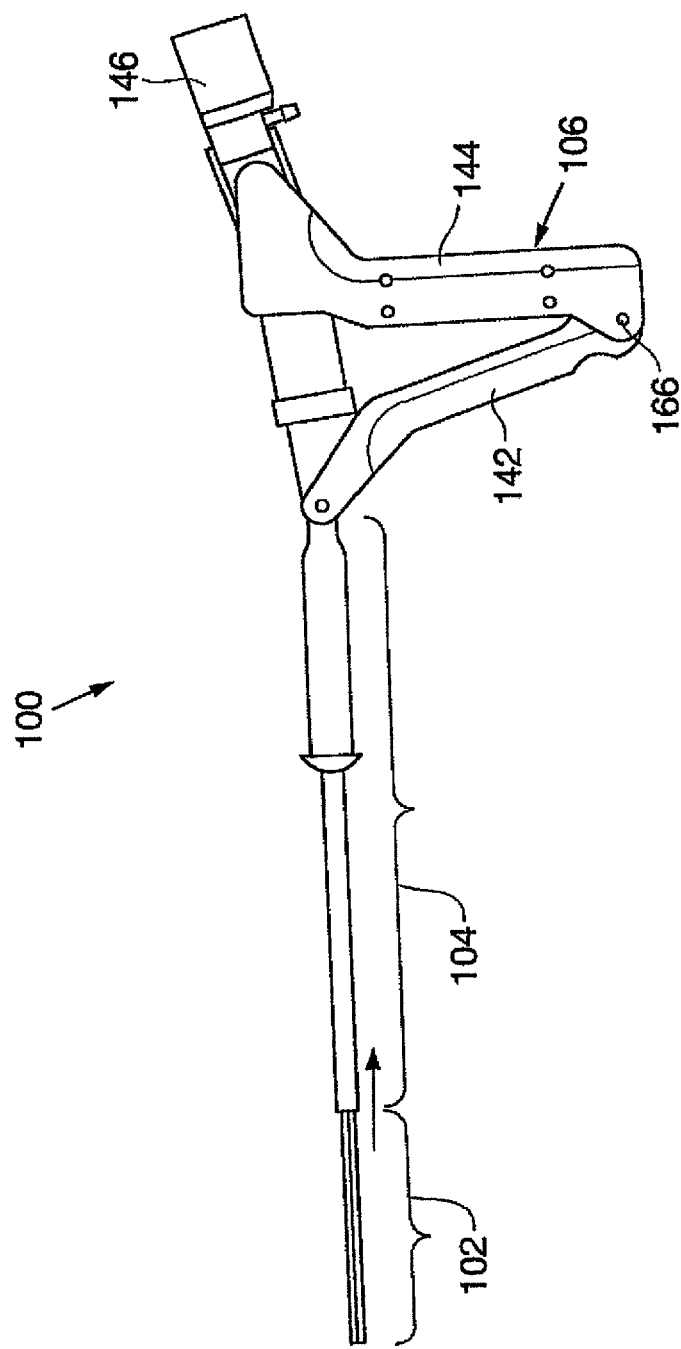
FIG. 22 is a side elevation view of the ablation device of FIG. 21, showing the array in the deployed state.
Figure 33:
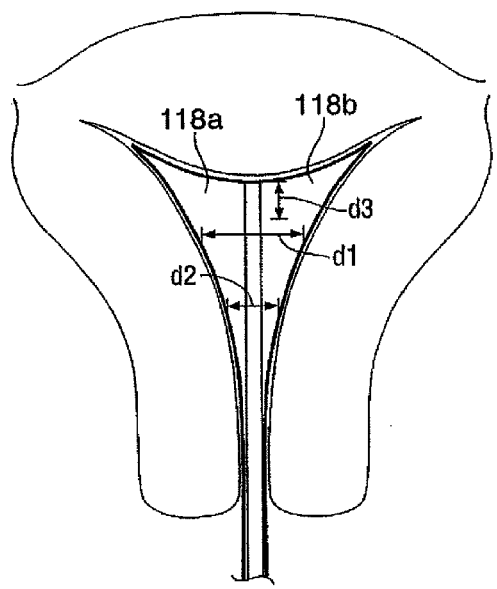
FIG. 33 illustrates placement of the applicator head according to the present invention in a uterine cavity.
Figure 35:
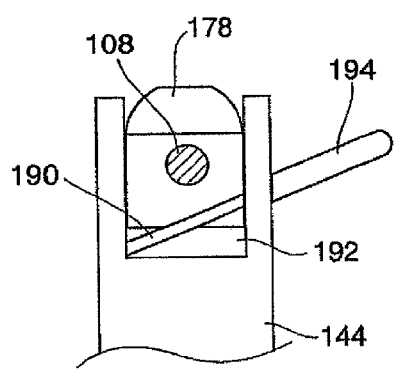
FIG. 35 is a front elevation view of the upper portion of the proximal handle grip taken along the plane designated 35-35 in FIG. 32B.
Figures 36A, 36B, 36C:
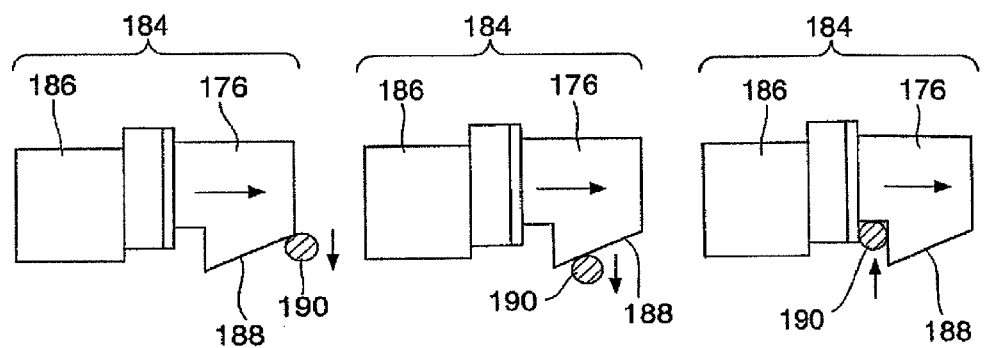
FIGS. 36A, 36B, and 36C are a series of side elevation views illustrating the heel member as it becomes engaged with the corresponding spring member.

Referring to FIGS. 21 and 22, the second embodiment includes an RF applicator head 102, a sheath 104, and a handle 106. As with the first embodiment, the applicator head 102 is slidably disposed within the sheath 104 (FIG. 21) during insertion of the device into the uterine cavity, and the handle 106 is subsequently manipulated to cause the applicator head 102 to extend from the distal end of the sheath 104 (FIG. 22) and to expand into contact with body tissue (FIG. 33).

RF Applicator Head

Figures 23, 24:
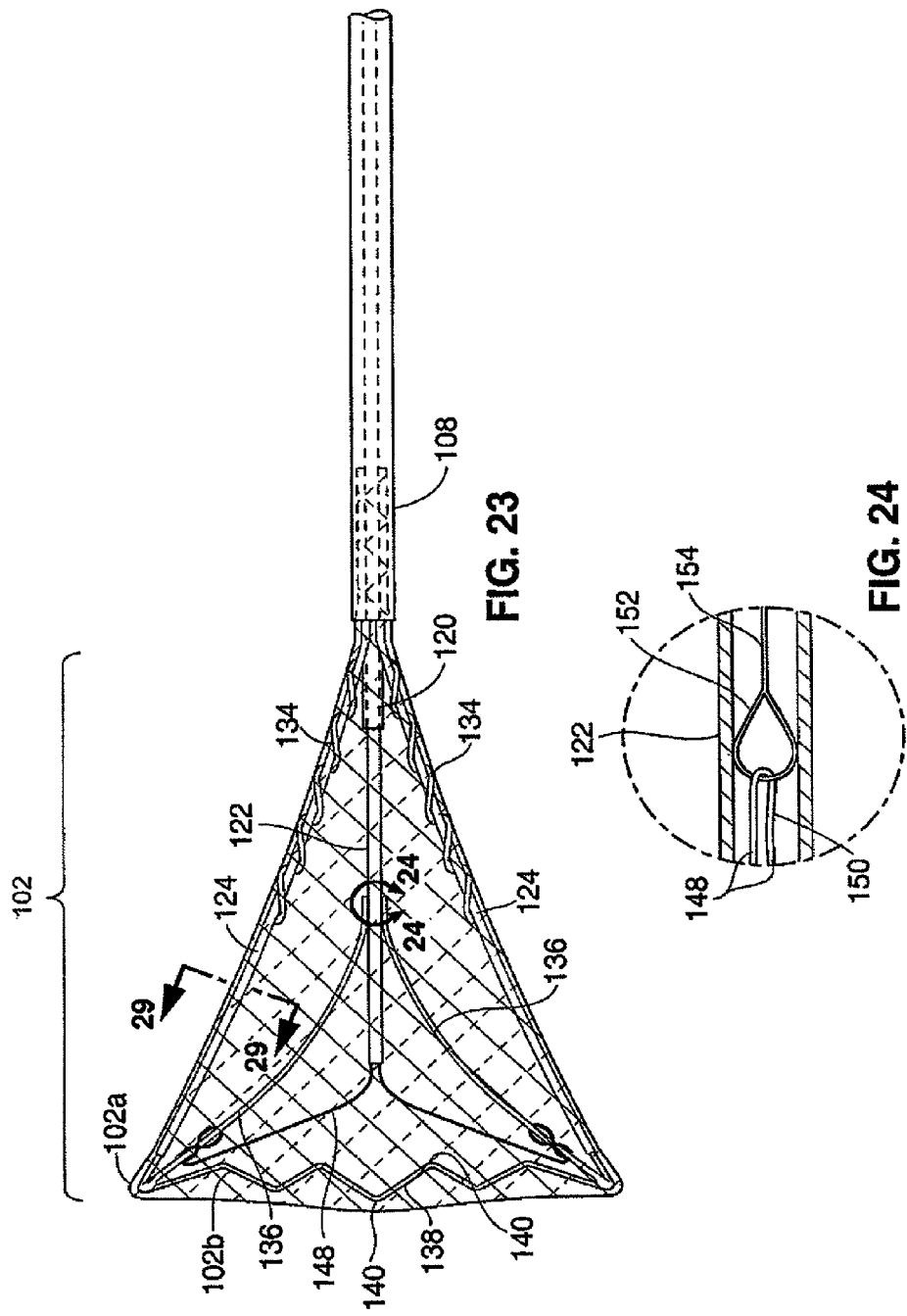
FIG. 23 is a top plan view of the applicator head of the apparatus of FIG. 21.
FIG. 24 is a cross-sectional top view of the encircled region designated 24 in FIG. 23.

Referring to FIG. 23, in which the sheath 104 is not shown for clarity, applicator head 102 extends from the distal end of a length of tubing 108 which is slidably disposed within the sheath 104. Applicator head 102 includes an external electrode array 102a and an internal deflecting mechanism 102b used to expand and tension the array for positioning into contact with the tissue.

Figure 25A:
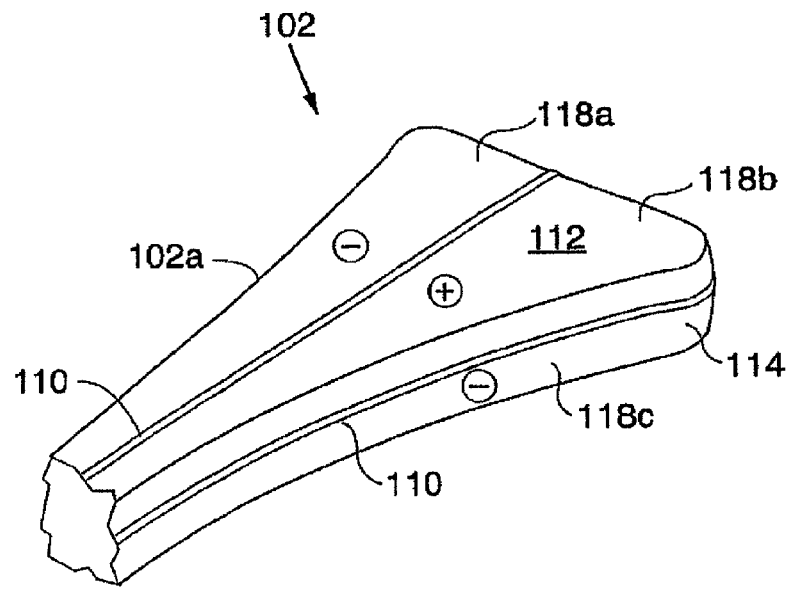
FIG. 25A is a perspective view of the electrode array of FIG. 23.
Figure 25B:
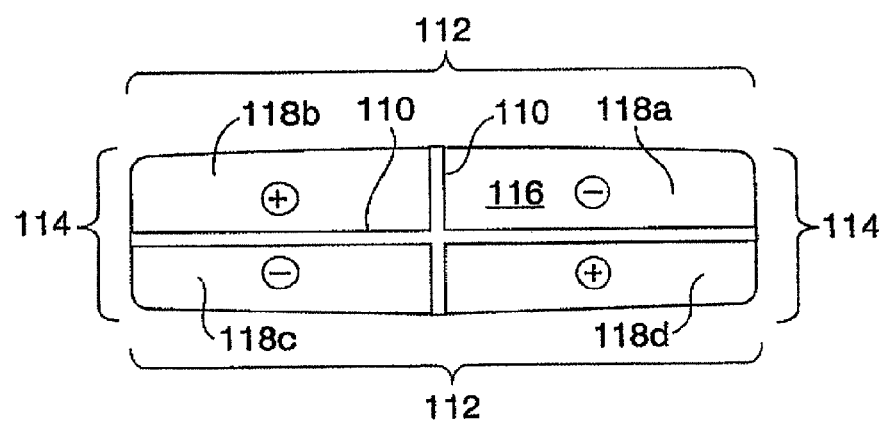
FIG. 25B is a distal end view of the applicator head of FIG. 30A.
Figure 26A:
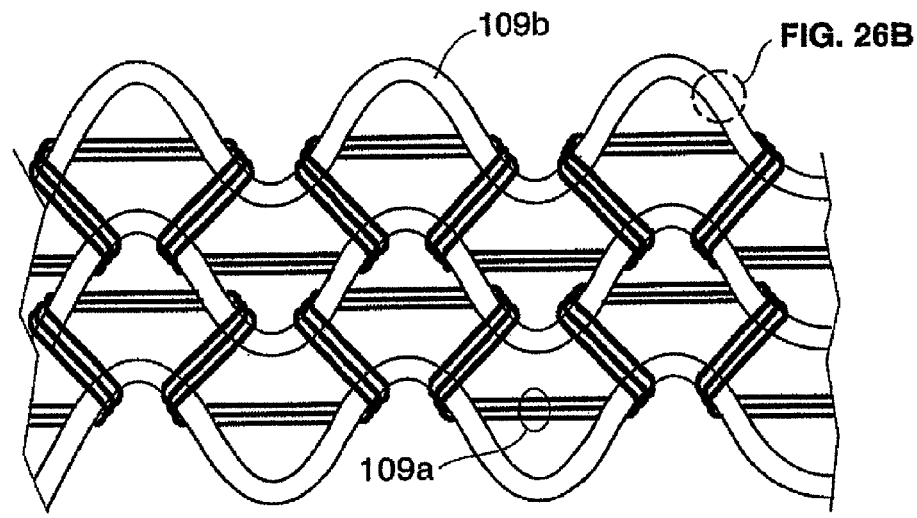
FIG. 26A is a plan view of a knit that may be used to form the applicator head.
Figure 26B:
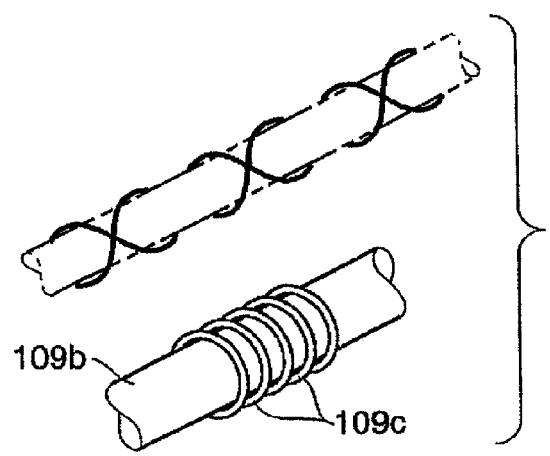
FIG. 26B is a perspective view of a strand of nylon-wrapped spandex of the type that may be used to form the knit of FIG. 26A.

Referring to FIGS. 25A and 25B, the array 102a of applicator head 102 is formed of a stretchable metallized fabric mesh which is preferably knitted from a nylon and spandex knit plated with gold or other conductive material. In one array design, the knit (shown in FIGS. 26A and 26B) is formed of three monofilaments of nylon 109a knitted together with single yarns of spandex 19b. Each yarn of spandex 109b has a double helix 109c of five nylon monofilaments coiled around it.

This knit of elastic (spandex) and inelastic (nylon) yarns is beneficial for a number of reasons. For example, knitting elastic and relatively inelastic yarns allows the overall deformability of the array to be pre-selected.

The mesh is preferably constructed so as to have greater elasticity in the transverse direction (T) than in the longitudinal direction (L). In a preferred mesh design, the transverse elasticity is on the order of approximately 300% whereas the longitudinal elasticity is on the order of approximately 100%. The large transverse elasticity of the array allows it to be used in a wide range of uterine sizes.

Another advantage provided by the combination of elastic and relatively inelastic yarns is that the elastic yarns provide the needed elasticity to the array while the relatively inelastic yarns provide relatively non-stretchable members to which the metallization can adhere without cracking during expansion of the array. In the knit configuration described above, the metallization adheres to the nylon coiled around the spandex. During expansion of the array, the spandex elongates and the nylon double helix at least partially elongates from its coiled configuration.

One process which may be used to apply the gold to the nylon/spandex knit involves plating the knit with silver using known processes which involve application of other materials as base layers prior to application of the silver to ensure that the silver will adhere. Next, the insulating regions 110 (described below) are etched onto the silver, and afterwards the gold is plated onto the silver. Gold is desirable for the array because of it has a relatively smooth surface, is a very inert material, and has sufficient ductility that it will not crack as the nylon coil elongates during use.

Figure 27A:
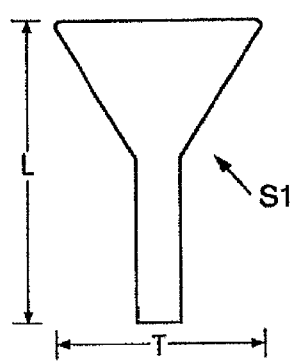
FIGS. 27A, 27B, 27C are top plan views illustrating triangular, parabolic, and rectangular mesh shapes for use as electrode arrays according to the present invention.
Figure 27B:
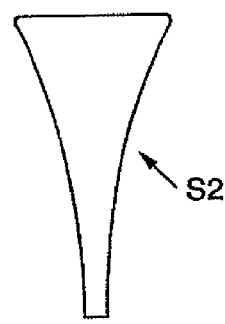
Figure 27C:
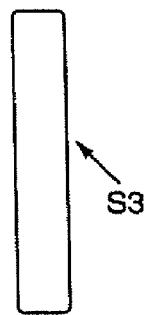
Figure 28:
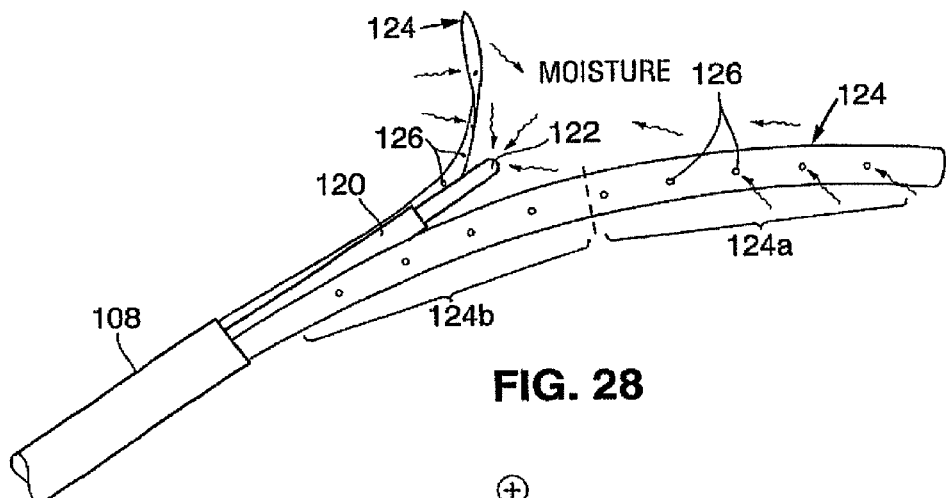
FIG. 28 is a perspective view showing the flexures and hypotube of the deflecting mechanism of the applicator head of FIG. 23.

The mesh may be configured in a variety of shapes, including but not limited to the triangular shape S1, parabolic S2, and rectangular S3 shapes shown in FIGS. 27A, 27B and 27C, respectively.

Turning again to FIGS. 25A and 25B, when in its expanded state, the array 102a includes a pair of broad faces 112 spaced apart from one another. Narrower side faces 114 extend between the broad faces 112 along the sides of the applicator head 102, and a distal face 116 extends between the broad faces 112 at the distal end of the applicator head 102.

Insulating regions 110 are formed on the applicator head to divide the mesh into electrode regions. The insulated regions 110 are preferably formed using etching techniques to remove the conductive metal from the mesh, although alternate methods may also be used, such as by knitting conductive and non-conductive materials together to form the array.

The array may be divided by the insulated regions 110 into a variety of electrode configurations. In a preferred configuration the insulating regions 110 divide the applicator head into four electrodes 118a-118d by creating two electrodes on each of the broad faces 112. To create this four-electrode pattern, insulating regions 110 are placed longitudinally along each of the broad faces 112 as well as along the length of each of the faces 114, 116. The electrodes 118a-118d are used for ablation and, if desired, to measure tissue impedance during use.

Deflecting mechanism 102b and its deployment structure is enclosed within electrode array 102a. Referring to FIG. 23, external hypotube 120 extends from tubing 108 and an internal hypotube 122 is slidably and co-axially disposed within hypotube 120. Flexures 124 extend from the tubing 108 on opposite sides of external hypotube 120. A plurality of longitudinally spaced apertures 126 (FIG. 28) are formed in each flexure 124. During use, apertures 126 allow moisture to pass through the flexures and to be drawn into exposed distal end of hypotube 120 using a vacuum source fluidly coupled to hypotube 120.

Figure 29:
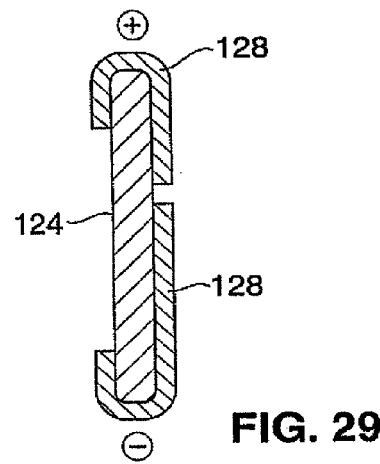
FIG. 29 is a cross-section view of a flexure taken along the plane designated 29-29 in FIG. 23.

Each flexure 124 preferably includes conductive regions that are electrically coupled to the array 102a for delivery of RF energy to the body tissue. Referring to FIG. 29, strips 128 of copper tape or other conductive material extend along opposite surfaces of each flexure 124. Each strip 128 is electrically insulated from the other strip 128 by a non-conductive coating on the flexure. Conductor leads (not shown) are electrically coupled to the strips 128 and extend through tubing 108 (FIG. 23) to an electrical cord 130 (FIG. 21) which is attachable to the RF generator.

During use, one strip 128 on each conductor is electrically coupled via the conductor leads to one terminal on the RF generator while the other strip is electrically coupled to the opposite terminal, thus causing the array on the applicator head to have regions of alternating positive and negative polarity.

The flexures may alternatively be formed using a conductive material or a conductively coated material having insulating regions formed thereon to divide the flexure surfaces into multiple conductive regions. Moreover, alternative methods such as electrode leads independent of the flexures 124 may instead be used for electrically connecting the electrode array to the source of RF energy.

It is important to ensure proper alignment between the conductive regions of the flexures 124 (e.g. copper strips 128) and the electrodes 118a-118d in order to maintain electrical contact between the two. Strands of thread 134 (which may be nylon) (FIG. 23) are preferably sewn through the array 102a and around the flexures 124 in order to prevent the conductive regions 128 from slipping out of alignment with the electrodes 118a-118d. Alternate methods for maintaining contact between the array 102a and the conductive regions 128 include using tiny bendable barbs extending between the flexures 124 and the array 102a to hook the array to the conductive regions 128, or bonding the array to the flexures using an adhesive applied along the insulating regions of the flexures.

Referring again to FIG. 23, internal flexures 136 extend laterally and longitudinally from the exterior surface of hypotube 122. Each internal flexure 136 is connected at its distal end to one of the flexures 124 and a transverse ribbon 138 extends between the distal portions of the internal flexures 136. Transverse ribbon 138 is preferably pre-shaped such that when in the relaxed condition the ribbon assumes the corrugated configuration shown in FIG. 23 and such that when in a compressed condition it is folded along the plurality of creases 140 that extend along its length. Flexures 124, 136 and ribbon 138 are preferably an insulated spring material such as heat treated 17-7 PH stainless steel.

The deflecting mechanism is preferably configured such that the distal tips of the flexures 124 are sufficiently flexible to prevent tissue puncture during deployment and/or use. Such an atraumatic tip design may be carried out in a number of ways, such as by manufacturing the distal sections 124a (FIG. 28) of the flexures from a material that is more flexible than the proximal sections 124b. For example, flexures 124 may be provided to have proximal sections formed of a material having a modulus of approximately 28×106 psi and distal sections having a durometer of approximately 72 D.

Figure 30:
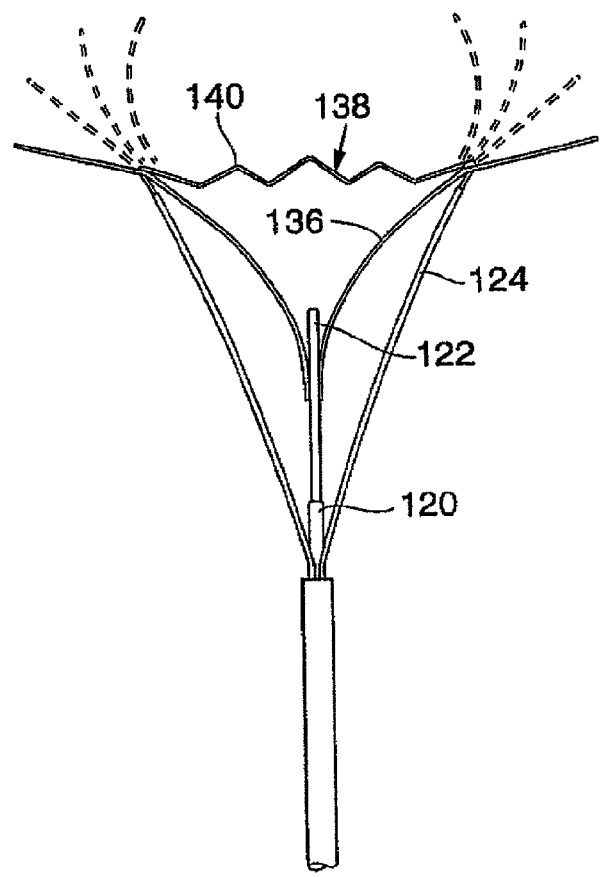
FIG. 30 is a top plan view illustrating the flexure and spring arrangement of an alternative configuration of a deflecting mechanism for an applicator head according to the present invention.

Alternatively, referring to FIG. 30, the flexures 124 may be joined to the internal flexures 136 at a location more proximal than the distal tips of the flexures 124, allowing them to move more freely and to adapt to the contour of the surface against which they are positioned (see dashed lines in FIG. 30). Given that uterine sizes and shapes vary widely between women, the atraumatic tip design is further beneficial in that it allows the device to more accurately conform to the shape of the uterus in which it is deployed while minimizing the chance of injury.

The deflecting mechanism formed by the flexures 124, 136, and ribbon 138 forms the array into the substantially triangular shape shown in FIG. 23, which is particularly adaptable to most uterine shapes. As set forth in detail below, during use distal and proximal grips 142, 144 forming handle 106 are squeezed towards one another to withdraw the sheath and deploy the applicator head. This action results in relative rearward motion of the hypotube 120 and relative forward motion of the hypotube 122. The relative motion between the hypotubes causes deflection in flexures 124, 136 which deploys and tensions the electrode array 102a.

Measurement Device

The ablation device according to the second embodiment includes a measurement device for easily measuring the uterine width and for displaying the measured width on a gauge 146 (FIG. 21). The measurement device utilizes non-conductive (e.g. nylon) suturing threads 148 that extend from the hypotube 122 and that have distal ends attached to the distal portion of the deflecting mechanism (FIG. 23). As shown in FIG. 24, threads 148 are preferably formed of a single strand 150 threaded through a wire loop 152 and folded over on itself. Wire loop 152 forms the distal end of an elongate wire 154 which may be formed of stainless steel or other wire.

Figure 31:
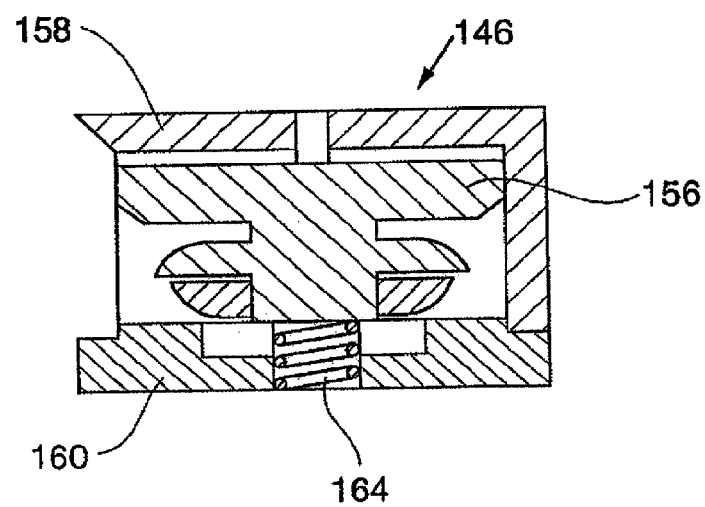
FIG. 31 is a cross-sectional side view of the bobbin portion of the apparatus of FIG. 21.

Referring to FIG. 31, wire 154 extends through the hypotube 122 and is secured to a rotatable bobbin 156. The rotatable bobbin 156 includes a dial face 158 preferably covered in a clear plastic. As can be seen in FIG. 32b, dial face 158 includes calibration markings corresponding to an appropriate range of uterine widths. The bobbin is disposed within a gauge housing 160 and a corresponding marker line 162 is printed on the gauge housing. A torsion spring 164 provides rotational resistance to the bobbin 156.

Expansion of the applicator head 102 during use pulls threads 148 (FIG. 23) and thus wire 154 (FIG. 24) in a distal direction. Wire 154 pulls against the bobbin 156 (FIG. 31), causing it to rotate. Rotation of the bobbin positions one of the calibration markings on dial face 158 into alignment with the marker line 162 (FIG. 32B) to indicate the distance between the distal tips of flexures 124 and thus the uterine width.

The uterine width and length (as determined using a conventional sound or other means) are preferably input into an RF generator system and used by the system to calculate an appropriate ablation power as will be described below. Alternately, the width as measured by the apparatus of the invention and length as measured by other means may be used by the user to calculate the power to be supplied to the array to achieve the desired ablation depth.

The uterine width may alternatively be measured using other means, including by using a strain gauge in combination with an A/D converter to transduce the separation distance of the flexures 124 and to electronically transmit the uterine width to the RF generator.

Control of Ablation Depth

The most optimal electrocoagulation occurs when relatively deep ablation is carried out in the regions of the uterus at which the endometrium is thickest, and when relatively shallower ablation is carried out in areas in which the endometrium is shallower. A desirable range of ablation depths includes approximately 2-3 mm for the cervical os and the cornual regions, and approximately 7-8 mm in the main body of the uterus where the endometrium is substantially thicker.

As discussed with respect to the first embodiment, a number of factors influence the ablation depth that can be achieved using a given power applied to a bipolar electrode array. These include the power supplied by the RF generator, the distance between the centers of adjacent electrodes ("center-to-center distance"), the electrode density (i.e., the porosity of the array fabric or the percent of the array surface that is metallic), the edge gap (i.e. the distance between the edges of adjacent electrode poles), and the electrode surface area. Other factors include blood flow (which in slower-ablating systems can dissipate the RF) and the impedance limit.

Certain of these factors may be utilized in the present invention to control ablation depth and to provide deeper ablation at areas requiring deeper ablation and to provide shallower regions in areas where deep ablation is not needed. For example, as center-to-center distance increases, the depth of ablation increases until a point where the center to center distance is so great that the strength of the RF field is too diffuse to excite the tissue. It can been seen with reference to FIG. 33 that the center to center distance d1 between the electrodes 118a, 118b is larger within the region of the array that lies in the main body of the uterus and thus contributes to deeper ablation. The center to center distance d2 between electrodes 118a, 118b is smaller towards the cervical canal where it contributes to shallower ablation. At the distal end of the device, the shorter center to center distances d3 extend between top and bottom electrodes 118b, 118c and 118a, 118d and again contribute to shallower ablation.

Naturally, because the array 102a expands to accommodate the size of the uterus in which it is deployed, the dimensions of the array 102a vary. One embodiment of the array 102a includes a range of widths of at least approximately 2.5-4.5 cm, a range of lengths of at least approximately 4-6 cm, and a density of approximately 35%-45%.

The power supplied to the array by the RF generator is calculated by the RF generator system to accommodate the electrode area required for a particular patient. As discussed above, the uterine width is measured by the applicator head 102 and displayed on gauge 146. The uterine length is measured using a sound, which is an instrument conventionally used for that purpose. It should be noted that calibration markings of the type used on a conventional sound device, or other structure for length measurement, may be included on the present invention to allow it to be used for length measurement as well.

The user enters the measured dimensions into the RF generator system using an input device, and the RF generator system calculates or obtains the appropriate set power from a stored look-up table using the uterine width and length as entered by the user. An EPROM within the RF generator system converts the length and width to a set power level according to the following relationship:

$$P = L \times W \times 5.5$$

Where P is the power level in watts, L is the length in centimeters, W is the width in centimeters, and 5.5 is a constant having units of watts per square centimeter.

Alternatively, the user may manually calculate the power setting from the length and width, or s/he may be provided with a table of suggested power settings for various electrode areas (as determined by the measured length and width) and will manually set the power on the RF generator accordingly.

Handle

Referring again to FIGS. 21 and 22, the handle 106 of the RF ablation device according to the second embodiment includes a distal grip section 142 and a proximal grip section 144 that are pivotally attached to one another at pivot pin 166.

Figure 34:
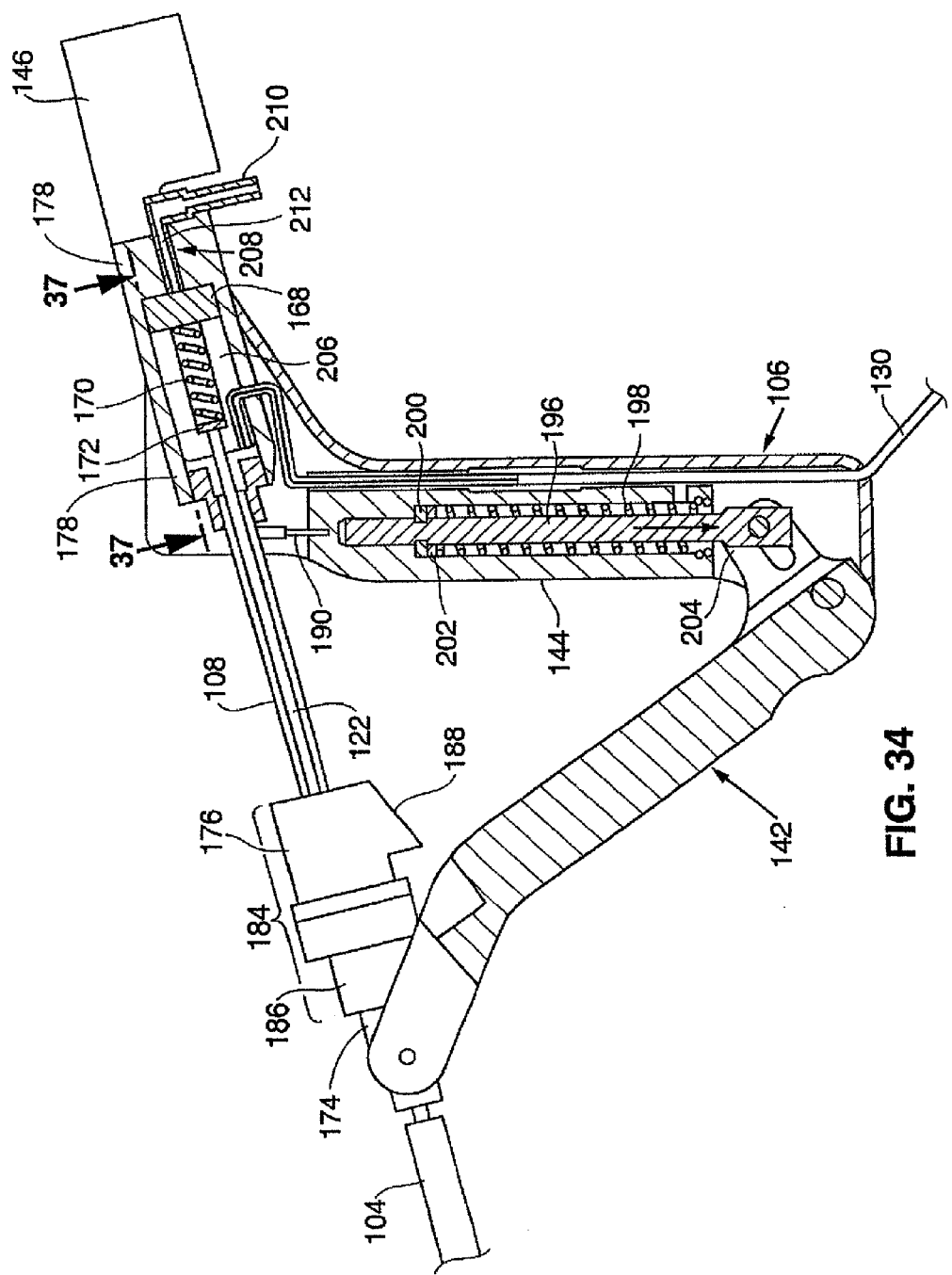
FIG. 34 is a side elevation view of the handle of the ablation apparatus of FIG. 21, showing portions of the apparatus in cross-section.

The proximal grip section 144 is coupled to the hypotube 122 (FIG. 23) via yoke 168, overload spring 170 and spring stop 172, each of which is shown in the section view of FIG. 34. The distal grip section 142 is coupled to the external hypotube 120 via male and female couplers 174, 176 (see FIGS. 32A and 32B). Squeezing the grip sections 142, 144 towards one another thus causes relative movement between the external hypotube 120 and the internal hypotube 122. This relative sliding movement results in deployment of the deflecting mechanism 102b from the distal end of the sheath and expansion of the array 102a to its expanded state.

Figure 32A:
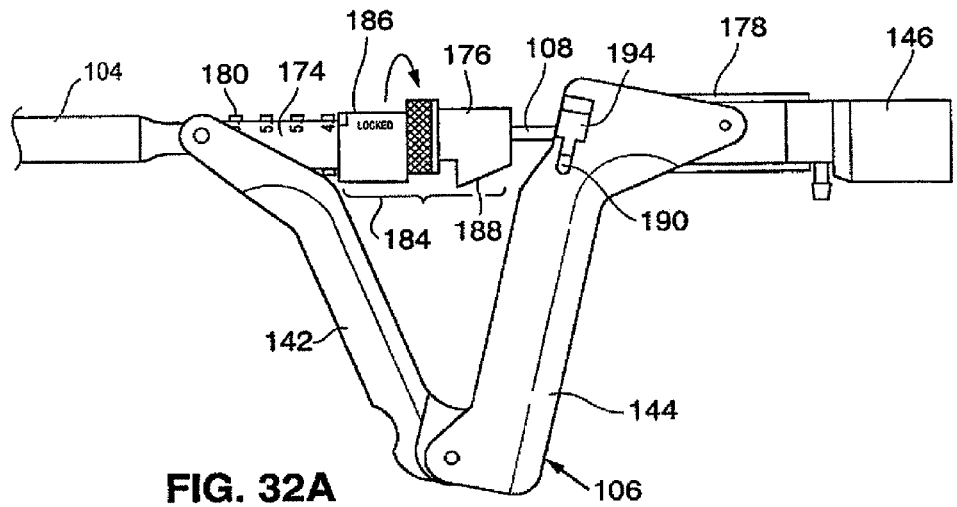
FIG. 32A is a side elevation view of the handle of the ablation device of FIG. 21.
Figure 32B:
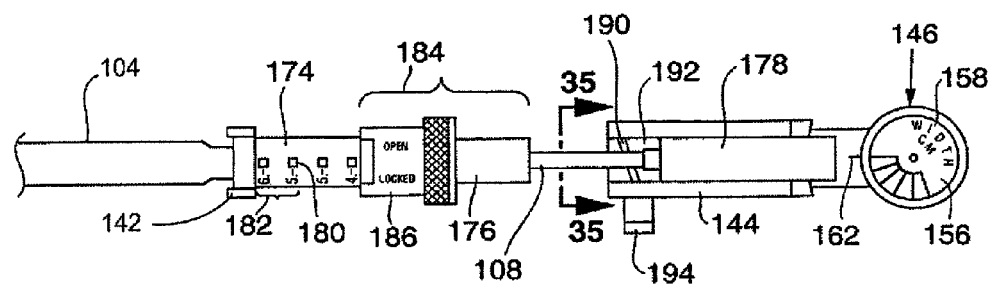
FIG. 32B is a top plan view of the handle of the ablation device of FIG. 21. For clarity, portions of the proximal and distal grips are not shown.

Referring to FIGS. 32A and B, rack 180 is formed on male coupler 174 and calibration markings 182 are printed adjacent the rack 180. The calibration markings 182 correspond to a variety of uterine lengths and may include lengths ranging from, for example, 4.0 to 6.0 cm in 0.5 cm increments.

A sliding collar 184 is slidably disposed on the tubing 108 and is slidable over male coupler 174. Sliding collar 184 includes a rotating collar 186 and a female coupler 176 that includes a wedge-shaped heel 188. A locking spring member 190 (FIGS. 32B and 35) extends across an aperture 192 formed in the proximal grip 144 in alignment with the heel 188. When the distal and proximal handle sections are squeezed together to deploy the array, the heel 188 passes into the aperture 192. Its inclined lower surface gradually depresses the spring member 190 as the heel moves further into the aperture 192. See FIGS. 36A and 36B. After passing completely over the spring member, the heel moves out of contact with the spring member. The spring member snaps upwardly thereby engaging the heel in the locked position. See FIG. 36C.

A release lever 194 (FIG. 35) is attached to the free end of the spring member 190. To disengage the spring lock, release lever 194 is depressed to lower spring member 190 so that the inclined heel can pass over the spring member and thus out of the aperture 192.

Referring again to FIGS. 32A and 32B, sliding collar 184 is configured to allow the user to limit longitudinal extension of the array 102a to a distance commensurate with a patient's predetermined uterine length. It does so by allowing the user to adjust the relative longitudinal position of male coupler 174 relative to the female coupler 176 using the rotating collar 186 to lock and unlock the female coupler from the rack 180 and the male coupler 174. Locking the female coupler to the rack 180 and male coupler 174 will limit extension of the array to approximately the predetermined uterine length, as shown on the calibration markings 182.

Once the uterine length has been measured using a conventional sound, the user positions sliding collar 184 adjacent to calibration marks 182 corresponding to the measured uterine length (e.g. 4.5 cm). Afterwards, the user rotates the collar section 186 to engage its internally positioned teeth with the rack 180. This locks the longitudinal position of the heel 188 such that it will engage with the spring member 190 on the proximal grip when the array has been exposed to the length set by the sliding collar.

The handle 106 includes a pair of spring assemblies which facilitate controlled deployment and stowage of the array 102a. One of the spring assemblies controls movement of the grips 142, 144 to automatically stow the array 102a into the sheath 104 when the user stops squeezing the grips 142, 144 towards one another. The other of the spring assemblies controls the transverse movement of the spring flexures 124 to the expanded condition by limiting the maximum load that can be applied to the deployment mechanism 102b.

FIG. 34 shows the distal and proximal grips 142 and 144 in partial cross-section. The first spring assembly for controlled stowage includes a handle return mandrel 196 that is slidably disposed within the proximal grip 144. A compression spring 198 surrounds a portion of the return mandrel 196, and a retaining ring 200 is attached to the mandrel 196 above the spring 198. A spring stop 202 is disposed between the spring 198 and the retaining ring.

The lowermost end of the return mandrel 196 is pivotally engaged by a coupling member 204 on distal grip 142. Relative movement of the grips 142, 144 towards one another causes the coupling member 204 to pull the return member downwardly with the proximal grip 144 as indicated by arrows. Downward movement of the mandrel 196 causes its retaining ring 200 and spring stop 202 to bear downwardly against the compression spring 198, thereby providing a movement which acts to rotate the grips 142, 144 away from one another. When tension against the grips 142, 144 is released (assuming that heel 188 is not locked into engagement with spring member 190) the grips rotate apart into the opened position as the compression spring 198 returns to the initial state, stowing the applicator head inside the sheath.

The second spring assembly for controlling array deployment is designed to control separation of the flexures. It includes a frame member 178 disposed over yoke 168, which is pivotally attached to proximal grip 144. Tubing 108 extends from the array 102a (see FIG. 23), through the sheath 104 and is fixed at its proximal end to the frame member 178. Hypotube 122 does not terminate at this point but instead extends beyond the proximal end of tubing 108 and through a window 206 in the frame member. Its proximal end 208 is slidably located within frame member 178 proximally of the window 206 and is fluidly coupled to a vacuum port 210 by fluid channel 212. Hypotube 120 terminates within the frame. Its proximal end is fixed within the distal end of the frame.

A spring stop 172 is fixed to a section of the hypotube within the window 206, and a compression spring 170 is disposed around the hypotube between the spring stop 172 and yoke 168. See FIGS. 32B and 34.

Figure 37A:
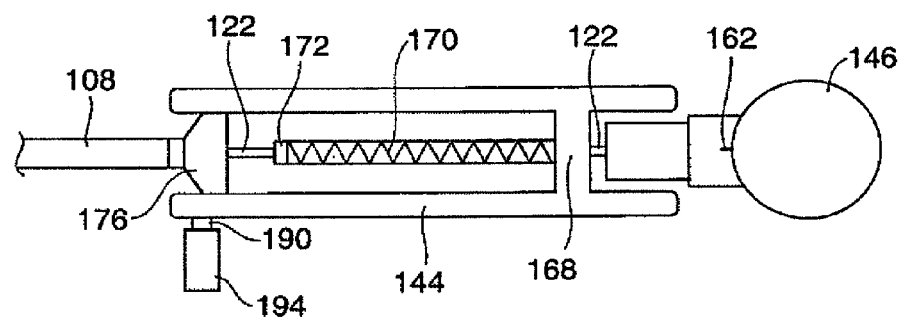
FIGS. 37A and 37B are cross-sectional top views of the frame member mounted on the proximal grip section, taken along the plane designated 37-37 in FIG. 34 and illustrating one of the load limiting features of the second embodiment.
Figure 37B:
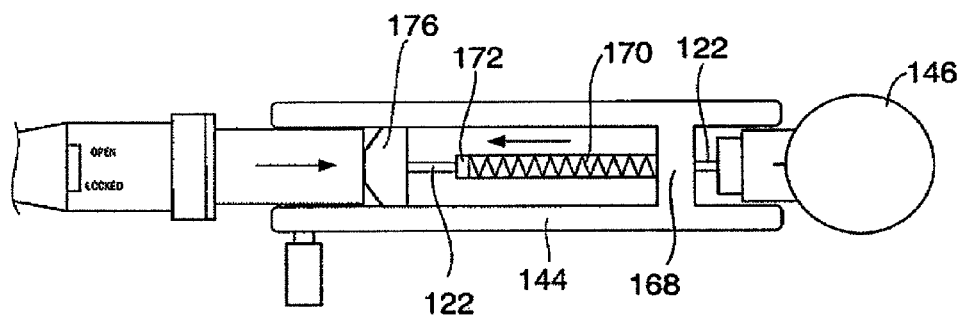

When the distal and proximal grips are moved towards one another, the relative rearward motion of the distal grip causes the distal grip to withdraw the sheath 104 from the array 102a. Referring to FIGS. 37A and 37B, this motion continues until female coupler 176 contacts and bears against frame member 178. Continued motion between the grips causes a relative rearward motion in the frame which causes the same rearward relative motion in external hypotube 120. An opposing force is developed in yoke 168, which causes a relative forward motion in hypotube 122. The relative motion between the hypotubes causes deflection in flexures 124, 136 which deflect in a manner that deploys and tensions the electrode array. Compression spring 170 acts to limit the force developed by the operator against hypotubes 120, 122, thus limiting the force of flexures 124, 136 acting on the array and the target tissue surrounding the array.

Referring to FIG. 21, collar 214 is slidably mounted on sheath 104. Before the device is inserted into the uterus, collar 214 can be positioned along sheath 104 to the position measured by the uterine sound. Once in position, the collar provides visual and tactile feedback to the user to assure the device has been inserted the proper distance. In addition, after the applicator head 102 has been deployed, if the patient's cervical canal diameter is larger than the sheath dimensions, the collar 214 can be moved distally towards the cervix, making contact with it and creating a pneumatic seal between the sheath and cervix.

Second Exemplary Embodiment—Operation

In preparation for ablating the uterus utilizing the second exemplary embodiment, the user measures the uterine length using a uterine sound device. The user next positions sliding collar 184 (FIG. 32B) adjacent to calibration marks 182 corresponding to the measured uterine length (e.g. 4.5 cm) and rotates the collar section 186 to engage its internally positioned teeth with the rack 180. This locks the longitudinal position of the heel 188 (FIG. 32A) such that it will engage with the spring member 190 when the array has been exposed to the length set by the sliding collar.

Next, with the grips 142, 144 in their resting positions to keep the applicator head 102 covered by sheath 104, the distal end of the device 100 is inserted into the uterus. Once the distal end of the sheath 104 is within the uterus, grips 142, 144 are squeezed together to deploy the applicator head 102 from sheath 104. Grips 142, 144 are squeezed until heel 188 engages with locking spring member 190 as described with respect to FIGS. 3BA through 36C.

At this point, deflecting mechanism 102b has deployed the array 102a into contact with the uterine walls. The user reads the uterine width, which as described above is transduced from the separation of the spring flexures, from gauge 146. The measured length and width are entered into the RF generator system 250 (FIG. 21) and used to calculate the ablation power.

Vacuum source 252 (FIG. 21) is activated, causing application of suction to hypotube 122 via suction port 210. Suction helps to draw uterine tissue into contact with the array 102.

Ablation power is supplied to the electrode array 102a by the RF generator system 250. The tissue is heated as the RF energy passes from electrodes 118a-d to the tissue, causing moisture to be released from the tissue. The vacuum source 252 helps to draw moisture from the uterine cavity into the hypotube 122. Moisture withdrawal is facilitated by the apertures 126 formed in flexures 124 by preventing moisture from being trapped between the flexures 124 and the lateral walls of the uterus.

If the RF generator 250 includes an impedance monitoring module, impedance may be monitored at the electrodes 118a-d and the generator may be programmed to terminate RF delivery automatically once the impedance rises to a certain level. The generator system may also or alternatively display the measured impedance and allow the user to terminate RF delivery when desired.

When RF delivery is terminated, the user depresses release lever 194 to disengage heel 188 from locking spring member 190 and to thereby allow grips 142, 144 to move to their expanded (resting) condition. Release of grips 142, 144 causes applicator head 102 to retract to its unexpanded condition and further causes applicator head 102 to be withdrawn into the sheath 104. Finally, the distal end of the device 100 is withdrawn from the uterus.

Two embodiments of ablation devices in accordance with the present invention have been described herein. These embodiments have been shown for illustrative purposes only. It should be understood, however, that the invention is not intended to be limited to the specifics of the illustrated embodiments but is defined only in terms of the following claims.

I claim:

1. A method for performing endometrial ablation comprising:
    transcervically positioning a distal portion of an ablation device into a uterus, the distal portion comprising an energy applicator, the energy applicator comprising a tissue contacting surface and an expandable-contractible carrying member, the expandable-contractible carrying member including first and second inner flexures and first and second outer flexures, the first and second outer flexures being coupled to an outer sleeve and the first and second inner flexures being coupled to an inner sleeve, the inner sleeve being slidably and coaxially disposed within the outer sleeve;
    actuating a handle coupled to a proximal portion of the ablation device to cause the carrying member to expand the energy applicator in the uterus, the handle comprising a proximal grip and a distal grip pivotally attached to one another at a pivot point, and wherein actuating the handle includes moving the proximal grip and the distal grip closer together while translating the inner sleeve relative to the proximal grip;
    actuating an inflation source to further expand the energy applicator in the uterus; and
    delivering energy through the energy applicator to thereby deliver energy to endometrial lining tissue of the uterus.

2. The method of claim 1 wherein the energy is delivered from at least one electrode carried by the applicator.

3. The method of claim 2, wherein the energy is delivered by bipolar electrodes carried by the applicator.

4. The method of claim 1, wherein the ablation device comprises an elongate introducer sheath.

5. A method as in claim 1, wherein the expandable-contractible carrying member comprises a balloon.

6. A method as in claim 5, wherein the ablation device comprises at least one inflation member having an inflation lumen fluidly coupled to an interior of the balloon, with a proximal end of the respective inflation member configured for fluidly coupling the respective inflation lumen with the inflation source.

7. A method as in claim 1, wherein the tissue contacting surface circumscribes the expandable-contractible carrying member.

8. A method as in claim 1, wherein the tissue contacting surface is expanded by eliminating compression of the carrying member followed by delivering a fluid from the inflation source to the applicator.

9. A method as in claim 1, wherein actuating the handle includes eliminating compression of the carrying member.

10. A method as in claim 9, wherein eliminating compression releases the carrying member to its natural size.

11. The method as in claim 1, further comprising:
    transcervically positioning an elongate hollow delivery sheath into a uterus, the delivery sheath having an axial lumen and an open distal end in communication with the lumen, the energy applicator slidably disposed within the delivery sheath lumen.

12. A method as in claim 1, wherein actuating the handle includes translating the inner sleeve proximally relative to the proximal grip.

13. A method as in claim 1, wherein actuating the inflation source includes passing a fluid from the inflation source to the energy applicator via the inner sleeve.

14. A method for performing endometrial ablation comprising:
    transcervically positioning a distal portion of an ablation device into a uterus, the distal portion comprising an energy applicator, the energy applicator comprising a tissue contacting member and an expandable-contractible carrying member, the expandable-contractible carrying member including first and second inner flexures and first and second outer flexures, the first and second outer flexures being coupled to an outer sleeve and the first and second inner flexures being coupled to an inner sleeve, the inner sleeve being slidably and coaxially disposed within the outer sleeve;
    actuating a handle coupled to a proximal portion of the ablation device to cause the carrying member to expand the energy applicator in the uterus, the handle comprising a proximal grip, a distal grip, and a spring, the proximal grip and the distal grip being pivotally attached to one another at a pivot point, wherein actuating includes moving the proximal grip and the distal grip closer together to cause the expandable-contractible carrying member to develop an expansion force against the tissue contacting member, wherein the expansion force is limited by the spring;
    actuating an inflation source to further expand the energy applicator in the uterus; and
    delivering energy through the energy applicator to thereby deliver energy to endometrial lining tissue of the uterus.

15. A method as in claim 14, wherein actuating the inflation source includes passing a fluid from the inflation source to the energy applicator via the inner sleeve.

16. A method as in claim 14 wherein the spring has a proximal portion fixed to the proximal grip and a distal portion fixed to the inner sleeve.

17. A method as in claim 14, wherein the expandable-contractible carrying member comprises a balloon.

18. A method as in claim 17, wherein the ablation device comprises at least one inflation member having an inflation lumen fluidly coupled to an interior of the balloon, with a proximal end of the respective inflation member configured for fluidly coupling the respective inflation lumen with the inflation source.

19. A method as in claim 14, wherein actuating the handle includes translating the inner sleeve proximally relative to the proximal grip.

* * * * *